United States Patent
Lippmann et al.

(10) Patent No.: US 10,920,193 B2
(45) Date of Patent: Feb. 16, 2021

(54) METHODS FOR EFFICIENT DERIVATION OF HUMAN MOTOR NEURONS FROM DIVERSE SPINAL REGIONS

(71) Applicant: Wisconsin Alumni Research Foundation, Madison, WI (US)

(72) Inventors: Ethan Scott Lippmann, Nashville, TN (US); Neha Sehgal, Philadelphia, PA (US); Randolph Scott Ashton, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 147 days.

(21) Appl. No.: 15/475,831

(22) Filed: Mar. 31, 2017

(65) Prior Publication Data
US 2017/0283774 A1 Oct. 5, 2017

Related U.S. Application Data

(60) Provisional application No. 62/317,115, filed on Apr. 1, 2016.

(51) Int. Cl.
*C12N 5/0797* (2010.01)

(52) U.S. Cl.
CPC ........ *C12N 5/0623* (2013.01); *C12N 2500/38* (2013.01); *C12N 2501/119* (2013.01); *C12N 2501/415* (2013.01); *C12N 2501/727* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 2007/0224650 A1* | 9/2007 | Jessell | C12N 5/0619 435/7.21 |
| 2010/0196332 A1* | 8/2010 | Wichterle | C12N 5/0619 424/93.7 |
| 2014/0134732 A1 | 5/2014 | Ashton et al. | |
| 2015/0010515 A1* | 1/2015 | Schoeler | C12N 5/0622 424/93.7 |
| 2016/0068806 A1 | 3/2016 | Ashton et al. | |

OTHER PUBLICATIONS

Morizane et al (J Neurosc Res 89: 117-126, 2011) (abstract).*
Lippmann et al, Termis-AM Conference, 3 pages, Dec. 2014, Abstract # O-520.*
Amoroso, et al. (2013). Accelerated high-yield generation of limb-innervating motor neurons from human stem cells. J. Neurosci. 33, 574-586.
Calder, et al., Retinoic Acid-Mediated Regulation of GLI3 Enables Efficient Motoneuron Derivation from Human ESCs in the Absence of Extrinsic SHH Activation. J. Neurosci. 35, 11462-11481 (2015).
Chen, et al. (2014). Modeling ALS with iPSCs reveals that mutant SOD1 misregulates neurofilament balance in motor neurons. Cell Stem Cell 14, 796-809.
Du, et al., Generation and expansion of highly pure motor neuron progenitors from human pluripotent stem cells. Nat. Commun. 6, 6626 (2015).
Karumbayaram, et al., Directed Differentiation of Human-Induced Pluripotent Stem Cells Generates Active Motor Neurons. Stem Cells 27, 806-811 (2009).
Kiskinis, et al. (2014). Pathways disrupted in human ALS motor neurons identified through genetic correction of mutant SOD1. Cell Stem Cell 14, 781-795.
Lee, et al. (2007). Directed differentiation and transplantation of human embryonic stem cell-derived motoneurons. Stem Cells 25, 1931-1939.
Li, et al. (2005). Specification of motoneurons from human embryonic stem cells. Nat. Biotechnol. 23, 215-221.
Li, et al. (2008). Directed differentiation of ventral spinal progenitors and motor neurons from human embryonic stem cells by small molecules. Stem Cells 26, 886-893.
Lian, et al., Previously demonstrated efficient β-catenin knockdown in the H9 ischcat2 line after 3 days of doxycycline treatment (Robust cardiomyocyte differentiation from human pluripotent stem cells via temporal modulation of canonical Wnt signaling. Proc. Natl. Acad. Sci. 109, E1848-E1857 (2012).
Lippmann, et al., Defined human pluripotent stem cell culture enables highly efficient neuroepithelium derivation without small molecule inhibitors, Stem Cells. 2014;32:1032-1042.
Lippmann, et al., Deterministic HOX Patterning in Human Pluripotent Stem Cell-Derived Neuroectoderm. Stem Cell Rep. 4, 632-644 (2015).
Maury, et al., Combinatorial analysis of developmental cues efficiently converts human pluripotent stem cells into multiple neuronal subtypes. Nat. Biotechnol. 33, 89-96 (2015).
Patani, et al. (2011). Retinoid-independent motor neurogenesis from human embryonic stem cells reveals a medial columnar ground state. Nat. Commun. 2, 214.
Qu, et al., High-efficiency motor neuron differentiation from human pluripotent stem cells and the function of Islet-1. Nat. Commun. 5, (2014).

* cited by examiner

*Primary Examiner* — Daniel E Kolker
*Assistant Examiner* — Aditi Dutt
(74) *Attorney, Agent, or Firm* — McDonnell Boehnen Hulbert & Berghoff LLP

(57) ABSTRACT

Described herein are chemically defined, adherent culture protocols for generating functional motor neurons characteristic of diverse hindbrain and spinal cord regions, with high efficiency.

15 Claims, 10 Drawing Sheets
(8 of 10 Drawing Sheet(s) Filed in Color)
Specification includes a Sequence Listing.

METHODS FOR EFFICIENT DERIVATION OF HUMAN MOTOR NEURONS FROM DIVERSE SPINAL REGIONS

CROSS-REFERENCE TO RELATED APPLICATIONS

This application claims the benefit of U.S. Provisional Patent Application No. 62/317,115, filed on Apr. 1, 2016, which is incorporated by reference in its entirety as if fully set forth herein.

STATEMENT REGARDING FEDERALLY SPONSORED RESEARCH OR DEVELOPMENT

This invention was made with government support under RD-83573701-0 awarded by the Environmental Protection Agency and NS082618 awarded by the National Institutes of Health. The government has certain rights in the invention.

BACKGROUND

Human pluripotent stem cells (hPSCs), including human embryonic stem cells (hESCs) and human induced pluripotent stem cells (hiPSCs), are powerful tools for studying human development and disease and may one day serve as a cell source for regenerative medicine. Significant advancements have been made in deriving neural stem cells from hPSCs and in their further differentiation to diverse neural lineages of the central nervous system (CNS) and peripheral nervous system (PNS). However, while researchers have made significant progress in differentiating human pluripotent stem cells (hPSCs) into neural cells patterned to specific regions of the anterior central nervous system (e.g. midbrain and forebrain), progress in effectively controlling hPSC specification to various segments of the hindbrain and spinal cord has been limited.

During development, rostrocaudal positional identity within the hindbrain and spinal cord is encoded by combinatorial expression of 39 HOX genes located within four paralogous genomic loci. HOX gene expression occurs in a spatially and temporally collinear manner. For example, motor neurons in the hindbrain primarily express rostral or 3' Hox paralogs (e.g. Hox1 to Hox4), and those in the spinal cord largely express caudal or 5' Hox paralogs (e.g. Hox4 to Hox13). Specifically in the spinal cord, HOX expression demarcates rostrocaudal segments, with Hox4 to Hox8 being primarily expressed in the cervical/brachial spinal cord, Hox9 being expressed in the thoracic spinal cord, and Hox10-13 being expressed in the lumbar/sacral spinal cord. Moreover, HOX expression can also encode segment-specific neural phenotypes. For example, the HOX expression profile in motor neurons regulates their subtype specification, columnar and pool segmentation, and innervation targeting of muscle groups.

Wnt/β-catenin signaling induces caudalization of hPSC-derived neural cells along the posterior CNS's rostrocaudal axis. FGF and Wnt/β-catenin signaling induce hPSCs to acquire a stable neuromesodermal phenotype, which progressively gains caudal identity by displaying full collinear HOX activation in a time-dependent manner. The neuromesodermal cells can then be subsequently differentiated into neural progenitors and neuronal subtypes of diverse and defined rostrocaudal regional identity at any point during the collinear HOX activation period. Wnt/β-catenin signaling also contributes to dorsoventral patterning of hPSCs and is implicated in motor neuron fate choices in the ventral spinal cord, particularly muscle innervation patterns; however, these mechanisms are less clear.

Motor neurons in the human spinal cord display diverse regional identities that convey efferent signals to distinct peripheral tissues and exhibit variable susceptibility to degenerative diseases. To date, cell culture-based differentiation protocols have predominantly generated spinal motor neurons characteristic of a single spinal cord region. Accordingly, a method to derive a fuller range of motor neurons from diverse spinal cord regions would be of great utility for disease modeling, regenerative therapy, and drug screening applications.

BRIEF SUMMARY OF THE INVENTION

U.S. patent application Ser. No. 14/496,796 (published as 2016/0068806), incorporated herein by reference as if set forth in its entirety, described methods and compositions permitting the generation of caudal lateral epiblasts, posterior neuroectodermal, and posterior neuroepithelial cell populations corresponding to specified positions along the rostrocaudal axis, based on the HOX gene expression patterns of such populations. The present invention relates to integrating dual patterning roles of Wnt/β-catenin beyond those disclosed in the '796 application to create a singular, chemically defined cell culture protocol for efficiently deriving ventral OLIG2$^+$ progenitors and post-mitotic spinal motor neurons from at least cervical, thoracic, and lumbar spinal cord regions.

FIGS. 1, 2, and 9 summarize in schematic form the approaches embodied in the invention. In general, the inventors here disclose protocols for differentiating Sox2$^+$, Brachyury$^+$ (Sox2$^+$/T$^+$) neuromesodermal progenitors into OLIG2$^+$/Nkx6.1$^+$/PAX6$^+$ ventral motor neuron progenitors having attributes of progenitors of at least cervical, thoracic, or lumbar spinal cord regions, followed by still further differentiation of such motor neuron progenitors into post-mitotic ISL1$^+$, HB9$^+$, and SMI32$^+$ motor neurons that, like the motor neuron progenitors, have attributes characteristics of at least cervical, thoracic, lumbar or spinal cord motor neurons.

The Sox2$^+$/T$^+$ neuromesodermal precursors can be, and are preferably, obtained by directing differentiation of human pluripotent stem cells, for example, in accordance with protocols disclosed in U.S. Ser. No. 14/496,796, incorporated herein by reference as if set forth in its entirety, as detailed infra. As this is a preferred approach for obtaining the neuromesodermal progenitors, references infra to the differentiation protocols, and to the timing of the protocols, is made with reference to a culture of hPSCs seeded at time 0 on day 0, although it is recognized that if the methods are initiated using cells having the indicated attributes of neuromesodermal progenitors, then the protocols can be adjusted to reflect the altered timeline relative to day 0 that would come about if the starting cells are neuromesodermal progenitors. As used herein, the term human "pluripotent stem cell" (hPSC) means a cell capable of continued self-renewal and capable, under appropriate conditions, of differentiating into cells of all three germ layers. Examples of hPSCs include human embryonic stem cells (hESCs) and human induced pluripotent stem cells (hiPSCs). As used herein, "hiPSCs" or "iPS cells" refer to cells that are substantially genetically identical to their respective differentiated somatic cell of origin and display characteristics similar to higher potency cells, such as ES cells, as described herein. The cells can be obtained by reprogramming non-pluripotent (e.g., multipotent or somatic) cells.

In the protocols, the cells are cultured in a neural differentiation base medium capable of promoting and supporting differentiation of human pluripotent stem cells towards a neural lineage (e.g., towards neuroectoderm and neuroepithelium). The base medium is supplemented, as described, with factors that direct differentiation as desired. Suitable base media include, but are not limited to, E6 medium, E5 medium, and E4 medium, each of which is described in U.S. Patent Publication No. 2014/0134732, incorporated herein by reference.

Starting hPSCs are cultured for about 1 day in the base medium and then are exposed for about 1 additional day to a fibroblast growth factor (FGF) in the medium. Then, the cells are passaged and replated at a conventional reseeding density of about $1.5 \times 10^5$ cells/cm$^2$. Thereafter, differentiation continues in the base medium in the presence of a Wnt/β-catenin signaling pathway agonist and an FGF at least until the cells acquire a Sox2$^+$/T$^+$ neuromesodermal progenitor phenotype and a ventral identity, characterized by expression of NKX6.1, a ventral transcription factor required in vivo for motor neuron development.

The duration and details of differentiation in the presence of the agonist and FGF can vary to allow for progressive collinear HOX gene expression, but in the disclosed protocols this differentiation step is followed in all cases by a transient exposure (e.g., for about 6 hours) of the differentiated NKX6.1$^+$ cells to a relatively higher concentration of the agonist (to about 6-9 μM from the 3 μM CHIR agonist, for example, typically used in the differentiation step) than in the preceding differentiation steps, and then by exposure of the transiently agonist-exposed NKX6.1$^+$ cells to an agonist of SHE (Sonic Hedgehog) signaling, which can include recombinant Shh or a small molecule agonist, and Retinoic Acid (RA), which induces neural, Pax6$^+$ differentiation until OLIG2$^+$, NKX6.1$^+$, PAX6$^+$ motor neuron progenitors having characteristics of motor neuron progenitor cells are present in the culture. The duration of this step of the protocol can vary and is typically in the range of about half a day to about four days.

Consistent with the disclosure in US patent application publication 2016/0068806, as the duration of exposure to Wnt/β-catenin signaling pathway agonist and an FGF increases, the attributes of the resulting cell types are increasingly caudal, with the shortest differentiation times before the transient agonist exposure (e.g., about 2 hours) yielding hindbrain-type, or longer times (e.g., about 48 hours) yielding cervical-type, motor neuron progenitors and motor neurons. Thoracic-type motor neuron progenitors are obtained if the initial exposure of the cells to the Wnt/β-catenin signaling pathway agonist continues for about an additional 48 hours, with the cells in culture being replated at higher density (e.g., about $4 \times 10^5$ cells/cm$^2$, to generate a confluent but not tightly packed cell monolayer, thereby maintaining cell contacts) when the cells approach confluence. Still more time and treatment is required to obtain lumbar-type motor neuron progenitors which can be obtained if, after the described higher-density replating, the cells are cultured for an additional 72 hours before the transient agonist exposure, the last 48 of which include Growth Differentiation Factor (GDF, which is involved with HOX-associated rostrocaudal differentiation) and dorsomorphin (DM, which counteracts the dorsalizing tendency of GDF). By carefully adjusting the duration and components of the differentiation step, it is expected that it will be possible to isolate additional types of motor neuron progenitors, and motor neurons, corresponding to those already recognized as associated with positions along the rostrocaudal axis or that are as yet unidentified.

Of note, the indicated cells obtained in the methods are obtained with particularly high efficiency, and represent significant percentages of the cells at each stage of culture, as detailed infra. Accordingly, the terminally differentiated motor neuron progenitors and post-mitotic neurons obtained in the methods can be obtained in amounts and in sufficient purity to warrant clinical and research use.

As will be appreciated by those of ordinary skill in the art, β-catenin signaling can be activated by modulating the function of one or more proteins that participate in the β-catenin signaling pathway to increase β-catenin expression levels or activity, T-cell factor/lymphoid enhancer factor (TCF/LEF) expression levels, or β-catenin-TCF/LEF-mediated transcriptional activity. An activator of β-catenin pathway signaling, as used herein, means an agent that directly or indirectly increases β-catenin signaling in a cell. Examples of such agents include, but are not limited to, any of agonists or activators of Wnt pathway signaling (e.g., Wnt3a), GSK3 kinase inhibitors, and agents for inducing β-catenin overexpression (e.g., overexpression vectors). In some embodiments, an activator of β-catenin pathway signaling is a small molecule that inhibits GSK3β phosphotransferase activity or GSK3β binding interactions. Suitable small molecule GSK3β inhibitors include, but are not limited to, CHIR 99021, CHIR 98014, BIO-acetoxime, BIO, LiCl, SB 216763, SB 415286, AR A014418, 1-Azakenpaullone, Bis-7-indolylmaleimide, and any combinations thereof in an amount or amounts effective to inhibit GSK3 phosphotransferase activity or GSK3 binding interactions. In some embodiments, any of CHIR99021, CHIR98014, and BIO-acetoxime are used to inhibit GSK3 in the differentiation methods described herein. In one embodiment, the small molecule GSK3β inhibitor used is CHIR99021 (sometimes referred to simply as CHIR) at a concentration ranging from about 1 μM to about 20 μM, e.g., about 2 μM, 3 μM, 4 μM, 5 μM 6 μM, 8 μM, 10 μM, 12 μM, 14 μM, 16 μM, or another concentration of CHIR99021 from about 1 μM to about 20 μM. In some embodiments, a concentration of about 3 μM is used. In one embodiment, an E6 medium contains CHIR99021 at a concentration of about 6 μM. In another embodiment, an E6 medium contains CHIR99021 at a concentration of about 9 μM. In another embodiment, the small molecule GSK3 inhibitor to be used is CHIR99021 at a concentration ranging from about 6 μM to about 9 μM, e.g., about 6.2 μM, 6.4 μM, 6.6 μM, 6.8 μM, 7 μM, 7.2 μM, 7.4 μM, 7.6 μM, 7.8 μM, 8 μM, 8.2 μM, 8.4 μM, 8.6 μM, 8.8 μM, 9 μM, or another concentration of CHIR99021 from about 6 μM to about 9 μM.

The FGF can be FGF8b or another FGF isoform used at a concentration ranging from about 20-500 ng/mL, which can be about 200 ng/mL.

Suitable activators of the hedgehog pathway include, but are not limited to purmorphamine (at a concentration from about 25 nM to about 300 nM), smoothened agonist (SAG), or CUR61414.

INCORPORATION BY REFERENCE

All publications, patents, and patent applications mentioned in this specification are incorporated by reference to the same extent as if each individual publication, patent, and patent application was specifically and individually indicated to be incorporated by reference.

Also incorporated into this provisional application as if set forth herein in its entirety is the manuscript attached as Exhibit A along with its associated figures, supplementary material, and list of cited citations.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein.

Figure 1:
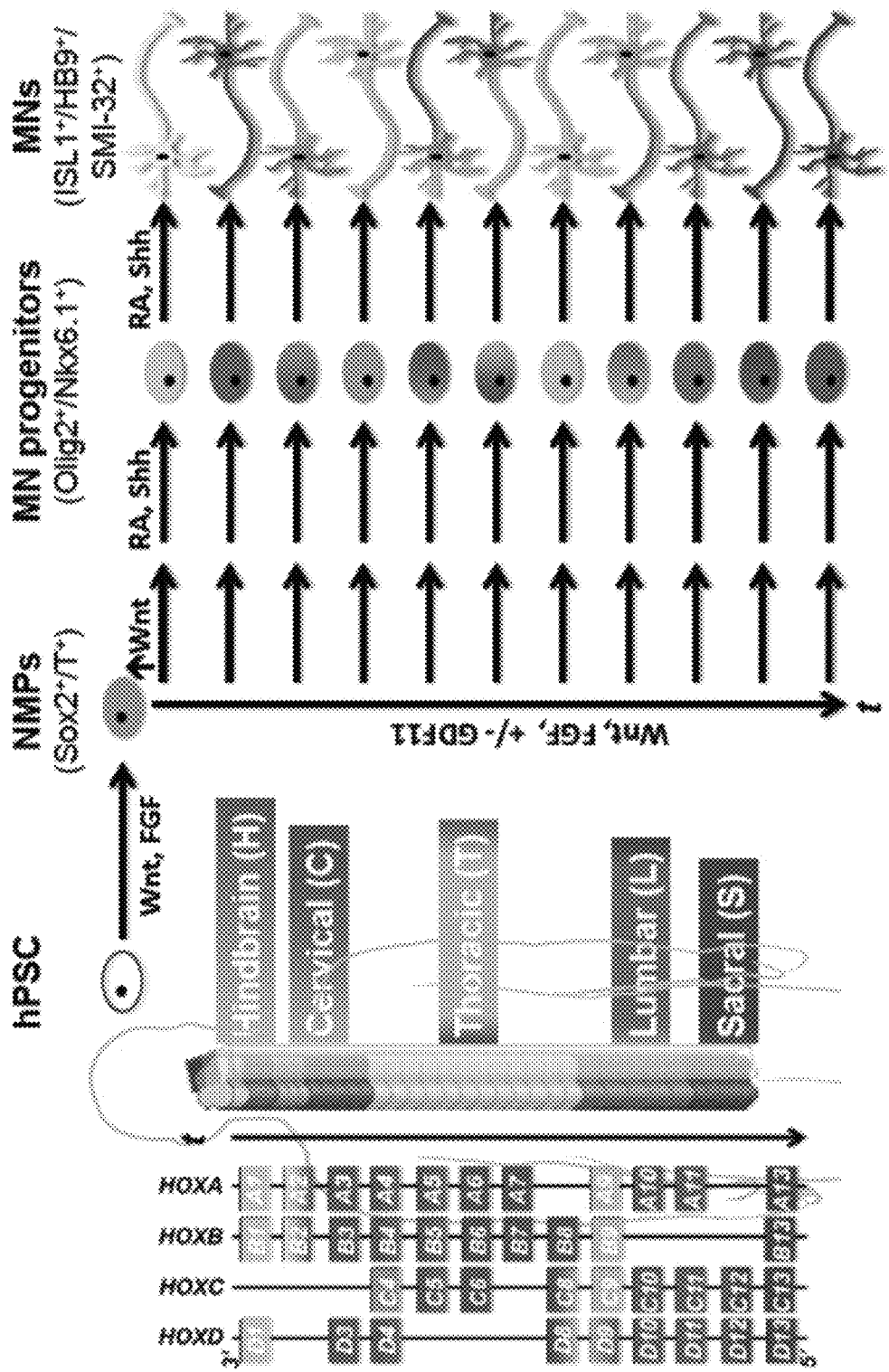
FIG. 1 schematically depicts differentiating hPSC through various stages to obtain motor neurons of various types.
Figure 2:
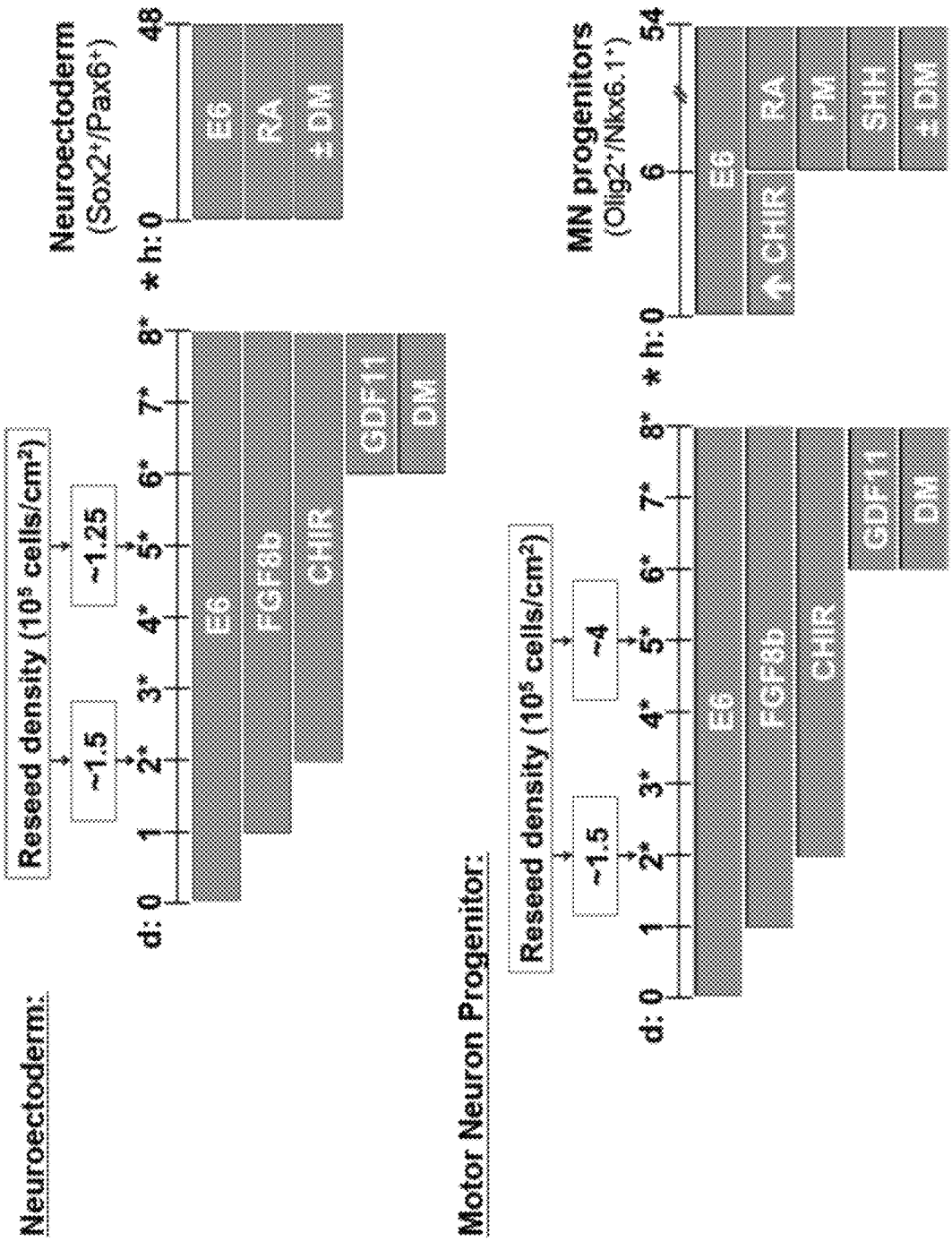
FIG. 2 provides a schematic summary of the basic disclosed differentiation methods at the bottom left of the FIG. The bottom right hand side depicts the transient Wnt activation and subsequent SHH signaling aspect of the methods, which can be implemented in the basic method at any time point marked with an asterisk, or at intermediate time points.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

II. Definitions

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

As used herein, "about" means within 10% of a stated concentration range or within 10% of a stated time frame.

As used herein, an effective or sufficient amount means an amount of an agent or a duration sufficient to evoke a specified cellular effect according to the present invention.

As used herein, the term human "pluripotent stem cell" (hPSC) means a cell capable of continued self-renewal and capable, under appropriate conditions, of differentiating into cells of all three germ layers. Examples of hPSCs include human embryonic stem cells (hESCs) and human induced pluripotent stem cells (hiPSCs). As used herein, "iPS cells" refer to cells that are substantially genetically identical to their respective differentiated somatic cell of origin and display characteristics similar to higher potency cells, such as ES cells, as described herein. The cells can be obtained by reprogramming non-pluripotent (e.g., multipotent or somatic) cells.

As used herein, "about" means within 10% of a stated concentration range or within 10% of a stated time frame.

"Activator of β-catenin pathway signaling," as used herein, means an agent that directly or indirectly increases canonical Wnt/β-catenin signaling in a cell. Examples of such agents include, but are not limited to, any of activators of Wnt pathway signaling (e.g., Wnt3a), GSK3 kinase inhibitors, and agents for inducing β-catenin overexpression. (e.g., overexpression vectors).

The term "defined culture medium" or "defined medium," as used herein, means that the chemical structure and quantity of each individual ingredient in the medium is definitively known and independently controlled.

As used herein, "a medium consisting essentially of" means a medium that contains the specified ingredients and that may contain additional ingredients that do not materially affect its basic characteristics.

As used herein, "effective amount" means an amount of an agent sufficient to evoke a specified cellular effect according to the present invention.

The terms "purified" or "enriched" cell populations are used interchangeably herein, and refer to cell populations, ex vivo, that contain a higher proportion of a specified cell type or cells having a specified characteristic than are found in vivo (e.g., in a tissue).

As used herein, an "mRNA expression profile" when referring to a cell population means the level of various RNA in the cell population as a whole, i.e., in an RNA sample extracted from the entire cell population, even though, there may be variation and deviation of mRNA expression profiles in individual cells or subpopulations from the cell population as a whole. For example if the mRNA expression profile of an isolated neuroepithelial cell population indicates that Hoxd10 mRNA is at a higher relative level than Hoxc9, this does not indicate that every individual cell in the population necessarily expresses Hoxd10 at a higher level than Hoxc9.

"Supplemented," as used herein, refers to a composition, e.g., a medium comprising a supplemented component (e.g., an FGF). For example a medium "further supplemented" with an FGF, refers to the medium comprising FGF, and not to the act of introducing the FGF to the medium.

As used herein, "viability" means the state of being viable. Pluripotent cells that are viable attach to the cell plate surface and do not stain with the dye propidium iodide absent membrane disruption. Short term viability relates to the first 24 hours after plating the cells in culture. Typically, the cells do not proliferate in that time.

As used herein, "pluripotency" means a cell's ability to differentiate into cells of all three germ layers.

Suitable quantitative methods for evaluating any of the above-markers are well known in the art and include, e.g., qRT-PCR, RNA-sequencing, RNA-blot, RNAse protection, and the like for evaluating gene expression at the RNA level. Quantitative methods for evaluating expression of markers at the protein level in cell populations are also known in the art. For example, flow cytometry, is typically used to determine the fraction of cells in a given cell population expressing (or not expressing) protein markers of interest.

The invention will be more fully understood upon consideration of the following non-limiting Examples. In the Examples, the ventralizing role of Wnt/β-catenin signaling was studied by systematically analyzing its effects at different points of hPSC motor neuron differentiation. Using a human embryonic stem cell (hESC) line harboring an inducible shRNA targeted to CTNNB1 (β-catenin), the knockdown of β-catenin during neural differentiation was demonstrated to reduce the efficiency of motor neuron derivation. This effect was traced to regulation of the ventral transcription factor NKX6.1, which is required for motor neuron development in vivo. Activation of Wnt/β-catenin using either soluble WNT3A or CHIR99021 (CHIR, a small molecule GSK3 inhibitor) rapidly induced NKX6.1 expression during hESCs neural differentiation, whereas activation of sonic hedgehog (SHH) or RA signaling had no effect on NKX6.1. Continuous activation of Wnt/β-catenin signaling could maintain NKX6.1 expression but inhibited the ability of RA and SHH to induce PAX6$^+$/OLIG2$^+$ motor neuron progenitors. However, transient upregulation of Wnt/β-catenin signaling, followed by SHH and RA treatment, efficiently generated NKX6.1$^+$/PAX6$^+$/OLIG2$^+$ motor neuron progenitor cultures. In general, the methods presented herein provide access to hPSC-derived motor neuron progenitors.

I. Methods

In various embodiments, the differentiation and specification of hPSCs into motor neuron progenitor cells is effected by culturing the PSC using various media in combination with the additives and timing regimen described herein.

In some embodiments, a method for generating motor neuron progenitor cells from hPSCs includes the steps of: (i) transiently exposing SOX2$^+$ and Brachyury$^+$ neuromesodermal progenitor cells cultured in a neural differentiation base medium that comprises FGF and a first concentration of a Wnt/β-catenin signaling pathway agonist to a second higher concentration of the agonist until NKX6.1$^+$ ventral progenitor cells are obtained; and (ii) culturing the NKX6.1$^+$ ventral progenitor cells in the neural differentiation base medium comprising a retinoid and at least one sonic hedgehog (SHH) signaling pathway agonist in the absence of the Wnt agonist until OLIG2$^+$, NKX6.1$^+$, and PAX6$^+$ motor neuron progenitor cells are obtained.

In some cases, neuromesodermal progenitor cells are transiently exposed to the higher concentration of the Wnt agonist for about 6 hours. In some cases, the Wnt/β-catenin signaling pathway agonist is CHIR99021, and wherein the first concentration is about 3 μM and the second higher concentration is in the range of about 6-9 μM. Without being bound by any particular theory or mode of action, it is believed that such a transient exposure or "boost" to a Wnt signaling agonist specifically enhances motor neuron progenitor derivation.

In some embodiments, NKX6.1$^+$ ventral progenitor cells obtained according to step (i) have a cervical identity or a hindbrain identity. For example, step (i) can yield NKX6.1$^+$ ventral progenitor cells having a cervical identity, generated with at least about 90% efficiency from the neuromesodermal progenitor cells. Step (ii) can generate OLIG2$^+$, NKX6.1$^+$, and PAX6$^+$ motor neuron progenitor cells with at least about 80% efficiency from the NKX6.1$^+$ ventral progenitor cells.

In some embodiments, the SHH signaling pathway agonist is selected from the group consisting of purmorphamine, SHH, and a combination thereof. Purmorphamine (PM) is a small molecule agonist of sonic hedgehog signaling.

As will be appreciated by those of ordinary skill in the art, β-catenin signaling can be activated by modulating the function of one or more proteins that participate in the β-catenin signaling pathway to increase β-catenin expression levels or activity, T-cell factor/lymphoid enhancer factor (TCF/LEF) expression levels, or β-catenin-TCF/LEF-mediated transcriptional activity.

In some embodiments, an activator of Wnt/β-catenin pathway signaling (e.g., a Wnt/β-catenin signaling pathway agonist) is a small molecule that inhibits GSK3β phosphotransferase activity or GSK3β binding interactions. Suitable small molecule GSK3β inhibitors include, but are not limited to, CHIR 99021, CHIR 98014, BIO-acetoxime, BIO, LiCl, SB 216763, SB 415286, AR A014418, 1-Azakenpaullone, Bis-7-indolylmaleimide, and any combinations thereof in an amount or amounts effective to inhibit GSK3 phosphotransferase activity or GSK3 binding interactions. In some embodiments, any of CHIR 99021, CHIR 98014, and BIO-acetoxime are used to inhibit GSK3 in the differentiation methods described herein. In one embodiment, the small molecule GSK3β inhibitor is used at a concentration ranging from about 1 μM to about 20 μM, e.g., about 2 μM, 3 μM, 4 μM, 5 μM 6 μM, 8 μM, 10 μM, 12 μM, 14 μM, 16 μM, or another concentration of CHIR99021 from about 1 μM to about 20 μM. In one embodiment, a culture medium comprises CHIR 99021 at a concentration of about 6 μM. In another embodiment, the small molecule GSK3 inhibitor to be used is CHIR 98014 at a concentration ranging from about 0.2 μM to about 2 μM, e.g., about 0.6 μM, 0.8 μM, 1 μM, 1.2 μM, 1.4 μM, 1.6 μM, or another concentration of CHIR98014 from about 0.2 μM to about 2 μM.

In some embodiments, an activator of β-catenin pathway signaling (e.g., a Wnt/β-catenin signaling pathway agonist) is a molecule that acts by disrupting the interaction of β-catenin with Axin, a member of the β-catenin destruction complex. Disruption of Axin-β-catenin interaction allows β-catenin to escape degradation by the destruction complex thereby increasing the net level of β-catenin to drive β-catenin signaling. Exemplary disruptors of the Axin-β-catenin destruction complex include, without limitation, 5-(Furan-2-yl)-N-(3-(1H-imidazol-1-yl)propyl)-1,2-oxazole-3-carboxamide ("SKL2001"), which is commercially available, e.g., as catalog no. 681667 from EMD4 Biosciences. An effective concentration of SKL2001 to activate β-Catenin signaling ranges from about 10 µM to about 100 µM, e.g., about 20 µM, 30 µM, 40 µM, 50 µM, 60 µM, 70 µM, 80 µM, 90 µM or another concentration of SKL2001 from about 10 µM to about 100 µM.

In further embodiments, an activator of β-catenin pathway signaling is a Wnt polypeptide ligand, e.g., Wnt 3a, Wnt 5a, Wnt 7a, Wnt 9b, and Wnt 10b.

In another aspect, provided herein is a method for generating post-mitotic motor neurons having a specified spinal cord regional identity. The method comprises or consists essentially of exposing the motor neuron progenitor cells obtained according to methods provided herein to a retinoid and to at least one SHH signaling pathway agonist in the neural differentiation base medium, and optionally exposing the motor neuron progenitor cells to an inhibitor of BMP signaling (e.g., dorsomorphin (DM), noggin) in the base medium, until SMI32$^+$, ISL1$^+$, and HB9$^+$ post-mitotic motor neurons having a specified spinal cord regional identity are obtained. Suitable inhibitors of BMP include, but are not limited to dorsomorphin, noggin, DMH1, and LDN193189. A suitable concentration of: dorsomorphin ranges from about 50 nM to about 1,000 nM (e.g., 200 nM); Noggin ranges from 25 ng/ml to about 400 ng/ml (e.g., 100 ng/ml); DMH1 ranges from about 20 nM to about 500 nM; and LDN193189 ranges from about 50 nM to about 1,000 nM.

In some embodiments, the motor neuron progenitor cells are obtained from neuromesodermal progenitor cells by culturing human pluripotent stem cells in the presence of a Wnt agonist and an FGF in the neural differentiation base medium until the neuromesodermal progenitor cells are obtained.

II. Compositions

An advantage of the media and methods described herein is the ability to specify the rostral-caudal and dorso-ventro axis identity of neuromesodermal progenitor cells differentiated from an hPSC line, which give rise to similarly patterned human motor neuron populations. This is reflected in the ability to obtain essentially unlimited quantities of isolated populations of neuroectodermal cells, neuroepithelial cells, or motor neurons having a Hox gene mRNA expression profile characteristic of a distinct position along the rostral-caudal axis.

In some embodiments described herein is a cell culture that includes any of the isolated human motor neuron progenitor cell populations or post-mitotic motor neurons described herein, and a neural differentiation base medium. In some embodiments, the neural differentiation base medium contains water, salts, amino acids, vitamins, a carbon source, a buffering agent, selenium, and insulin. One of skill in the art appreciates the efficiency of using a basal medium such as DMEM/F12 as starting material to prepare the disclosed neural differentiation media. The term "basal medium" as used herein means a minimal medium that contains essentially water, salts, amino acids, vitamins, a carbon source, and a buffering agent. Such basal medium components are known in the art, e.g., a carbon source can include glucose, fructose, maltose, and galactose. Other components that do not change the basic characteristic of the medium but are otherwise desirable can also be included, such as the pH indicator phenol red. For example, Dulbecco's Modified Eagle Medium: Nutrient Mixture F-12 (DMEM/F12) is a basal medium commonly used to make suitable growth media for mammalian cell culture.

In some embodiments the isolated cell populations described herein are substantially pure populations of motor neuron progenitor cells. As used herein, the terms "isolating" and "isolated" refer to separating, selecting, or enriching for a cell type of interest or subpopulation of cells from surrounding, neighboring, or contaminating cells or from cells of another type. As used herein, the term substantially pure refers to a population of cells that is at least about 75% (e.g., at least about 75%, 85%, 90%, 95%, 98%, 99% or more) pure, with respect to motor neuron progenitors making up a total cell population. In other words, the term substantially pure refers to a population of motor neuron progenitors of the present invention that contains fewer than about 20%, fewer than about 10%, or fewer than about 5% of non-motor neuron progenitors when directing differentiation to obtain cells of the motor neuron progenitors lineage. The term substantially pure also refers to a population of motor neuron progenitors of the present invention that contains fewer than about 20%, about 10%, or about 5% of non-motor neuron progenitors in an isolated population prior to any enrichment, expansion step, or differentiation step. Typically, a population comprising motor neuron progenitors obtained by the disclosed methods comprises a very high proportion of motor neuron progenitors. In some embodiments, the cell population comprises about 50% to about 99% motor neuron progenitors, e.g., about 52%, 55%, 67%, 70%, 72%, 75%, 80%, 85%, 90%, 95%, 98%, or another percent of motor neuron progenitors from about 50% to about 99% motor neuron progenitors.

In some embodiments the isolated cell populations described herein are substantially pure populations of post-mitotic motor neurons. In such cases, the term substantially pure refers to a population of cells that is at least about 75% (e.g., at least about 75%, 85%, 90%, 95%, 98%, 99% or more) pure, with respect to post-mitotic motor neurons making up a total cell population. In other words, the term substantially pure refers to a population of post-mitotic motor neurons of the present invention that contains fewer than about 20%, fewer than about 10%, or fewer than about 5% of non-post-mitotic motor neurons when directing differentiation to obtain cells of the motor neuron lineage. The term substantially pure also refers to a population of motor neuron progenitors of the present invention that contains fewer than about 20%, about 10%, or about 5% of non-post-mitotic motor neurons in an isolated population prior to any enrichment, expansion step, or differentiation step. Typically, a population comprising post-mitotic motor neurons obtained by the disclosed methods comprises a very high proportion of post-mitotic motor neurons. In some embodiments, the cell population comprises about 50% to about 99% post-mitotic motor neurons, e.g., about 52%, 55%, 67%, 70%, 72%, 75%, 80%, 85%, 90%, 95%, 98%, or another percent of post-mitotic motor neurons from about 50% to about 99% post-mitotic motor neurons.

In some embodiments the isolated cell populations described herein comprise cells (e.g., motor neuron progenitor cells, post-mitotic motor neurons) that are genetically modified cell populations. For example, the cell populations can be obtained by differentiation of a genetically modified hPSC line (e.g., a transgenic line, a "knock-in" line, or a "knock-out" line). Methods for establishing genetically modified hPSC lines are well known in the art. See, e.g., Sun et al (2012), *Biotechnol J.,* 7(9):1074-1087; and Chatterjee et al (2011), 5; (56); pg. 3110. Alternatively, the isolated cell populations can be genetically modified directly by transient transfection (e.g., transfection of plasmid expression vectors, oligonucleotides, RNAi, or modified mRNAs) or viral transduction. In some embodiments such cells are genetically modified with an expression cassette or exogenous RNA encoding a fluorescent reporter protein, a growth factor, an extracellular protein, or an antibody.

EXAMPLES

Example 1: Wnt/β-Catenin Regulates Ventral Transcription Factor NKX6.1 Expression During hPSC Motor Neuron Differentiation In the ventral neural tube, SHH signaling generates OLIG2$^+$ motor neuron progenitors that subsequently mature into post-mitotic ISL1$^+$ and/or HB9$^+$ motor neurons. To probe the role of Wnt/β-catenin signaling during this process in vitro, we utilized the H9 ishcat2 hESC line, which harbors a doxycycline-inducible shRNA against CTNNB1. Lian et al. previously demonstrated efficient β-catenin knockdown in the H9 ischcat2 line after 3 days of doxycycline treatment (Robust cardiomyocyte differentiation from human pluripotent stem cells via temporal modulation of canonical Wnt signaling. Proc. Natl. Acad. Sci. 109, E1848-E1857 (2012)).

Figures 3A, 3B, 3C, 3D:
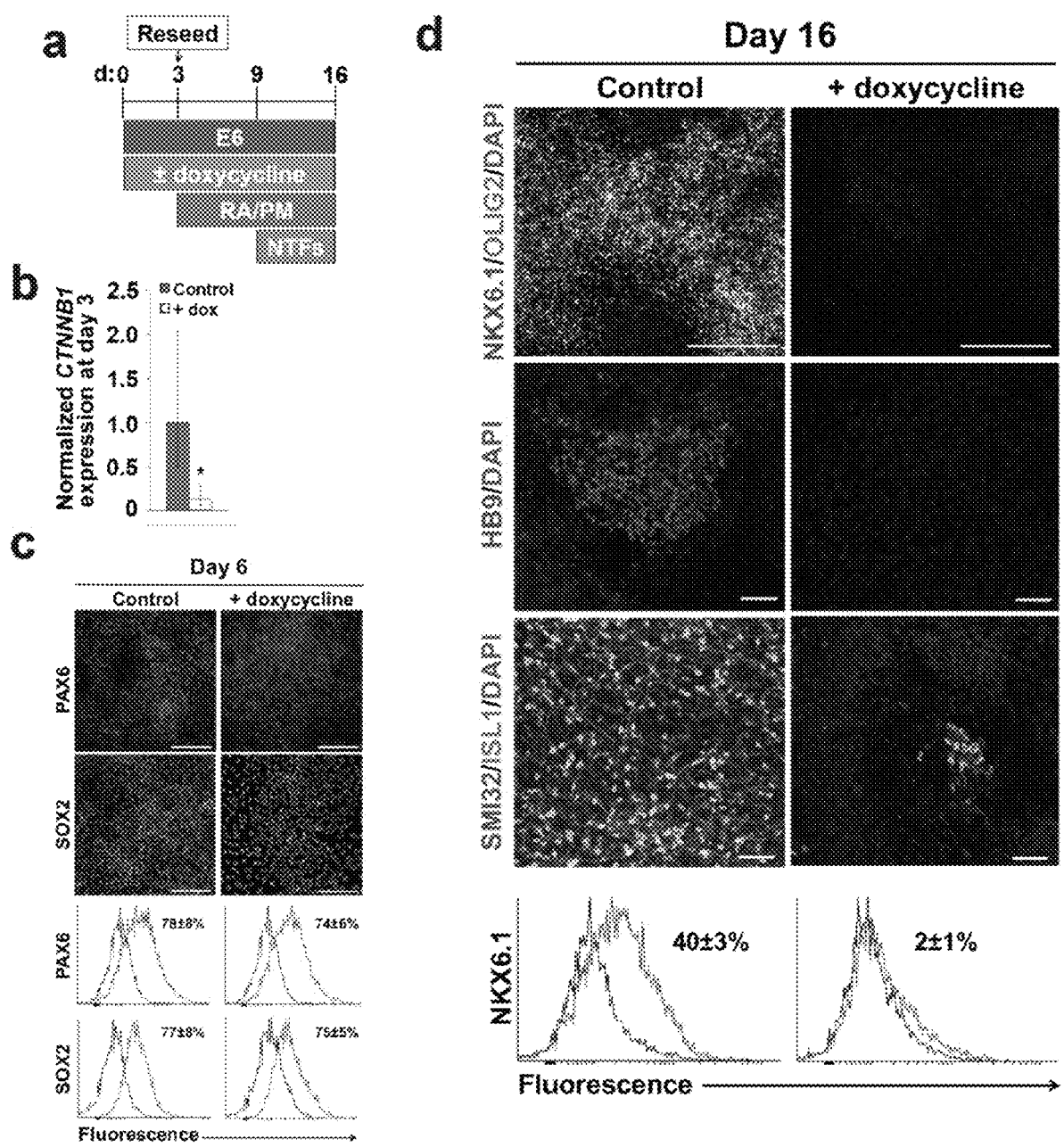
FIG. 3A shows a timeline for motor neuron differentiation using the H9 ishcat2 hESC line with or without 2 μg/mL doxycycline-induced shRNA knockdown of β-catenin. [RA] =1 μM, [PM]=100 nM, and NTFs indicate a neurotrophic factor cocktail of BDNF, GDNF, and cAMP.
FIG. 3B shows qPCR quantification of CTNNB1 relative to the RPS18 housekeeping gene at day 3. Data and error bars represent mean±S.D. from biological triplicates. *, p<0.05. Statistical significance was calculated using the student's unpaired t-test.
FIG. 3C shows immunocytochemical and flow cytometry evaluation of PAX6 and SOX2 expression at day 6 of differentiation. Percentages in flow histograms represent mean±S.D. calculated from four biological replicates. Scale bars, 100 μm.
FIG. 3D shows immunocytochemical and flow cytometry evaluation of NKX6.1, OLIG2, HB9, ISL1, and SMI32 expression at day 16 of differentiation. Percentages in flow histograms represent mean±S.D. calculated from four biological replicates (p<0.0001). Scale bars in top row of images, 200 μm; scale bars in all other panels, 50 μm.

Similarly, we induced β-catenin knockdown while differentiating the hESCs into motor neurons via E6 neural induction with RA (1 µM), purmorphamine (PM, a small molecule agonist of sonic hedgehog signaling; 100 nM), and neurotrophic factor treatment, as previously described (FIG. 3A). Doxycycline treatment, which reduced CTNNB1 expression by 87% ($p<0.05$, FIG. 3B) by day 3, did not affect neural induction as evidenced by prominent expression of the human spinal neuroectoderm markers PAX6 and SOX2 at day 6 (FIG. 3C). In contrast, doxycycline treatment led to markedly decreased expression of the ventral transcription factor NKX6.1, the motor neuron progenitor marker OLIG2, and post-mitotic motor neuron markers HB937, ISL138, and SMI32 reactive non-phosphorylated neurofilament heavy chain at day 16 (FIG. 3D). Quantification of NKX6.1 expression by flow cytometry revealed a decrease from 40±3% to 2±1% ($p<0.0001$) in response to β-catenin knockdown (FIG. 3D). These results suggest that endogenous Wnt/β-catenin signaling contributes to hPSC motor neuron differentiation.

Figures 4A, 4B, 4C, 4D, 4E, 4F, 4G, 4H:
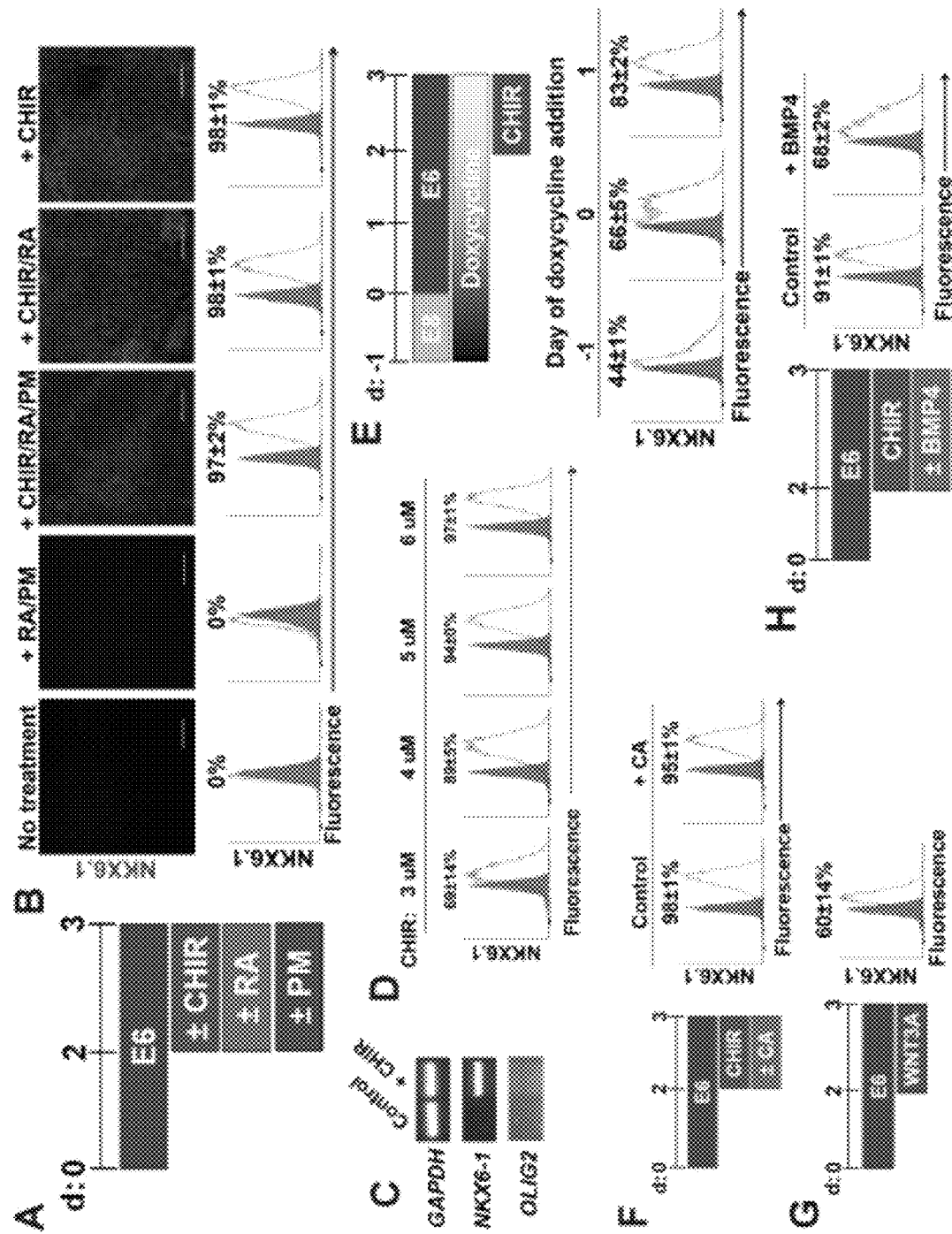
FIG. 4A shows a timeline for the H9 hESC differentiation in panels b-d.
FIG. 4B shows evaluation of NKX6.1 induction by immunocytochemistry and flow cytometry. [RA]=1 μM, [PM]=1 μM, and [CHIR]=6 μM. Scale bars, 100 μm.
FIG. 4C presents RT-PCR analysis of NKX6-1 and OLIG2 expression in the presence or absence of CHIR (6 μM).
FIG. 4D presents flow cytometry evaluation of NKX6.1 expression in response to varying doses of CHIR.
FIG. 4E shows flow cytometry evaluation of NKX6.1 expression after temporal β-catenin knockdown using the H9 ishcat2 line. Doxycycline treatment was initiated on the indicated day and continued until the cells were analyzed. [CHIR]=4 μM.
FIG. 4F shows flow cytometry evaluation of CHIR (6 μM)-mediated NKX6.1 induction in differentiating H9 hESC in the presence of Cyclopamine (CA; 5 μM).
FIGS. 4G and 4H show WNT3A (200 ng/mL) or (h) BMP4 (200 ng/mL). [CHIR]=4 μM. For all experiments, analyses were conducted at day 3. In all flow cytometry histograms, the gray curve is the IgG control and the red curve is the label of interest; percentages represent mean±S.D. (biological duplicates for all panels).

NKX6.1 is the earliest expressed marker in the motor neuron development cascade in vivo, so we examined its expression in response to Wnt/β-catenin, RA, and SHH signaling during hPSC motor neuron differentiation. H9 hESCs were differentiated in E6 medium for 2 days to initiate neural fate acquisition34 and then treated with combinations of RA, purmorphamine (PM, a small molecule agonist of SHH signaling), and CHIR for 24 h (FIG. 4A). Combined treatment with all factors could induce NKX6.1 expression within 24 h, and treatment with CHIR alone (6 µM) was sufficient to induce NKX6.1 but not OLIG2 gene expression and uniform NKX6.1 expression (98±1%) in a dose dependent manner (FIGS. 4A-4D). However, treatment with RA (1 µM) and PM (1 µM) did not induce NKX6.1 within 24 h (FIGS. 4A-4B). Using the H9 ishcat2 line, we observed that CHIR-mediated induction of NKX6.1 was β-catenin-dependent, as the optimal 3 days of shRNA-mediated CTNNB1 knockdown upstream of CHIR treatment was required to maximally reduce NKX6.1 induction to 44±1% (FIG. 4E). The correlation between NKX6.1 knockdown and days of doxycycline treatment was presumably due to the time delay for shRNA synthesis and subsequent gene knockdown in Tet-on systems. Since endogenous SHH activity, either occurring naturally during differentiation or in response to CHIR treatment, could potentially induce NKX6.1 expression, we treated neurally differentiating H9 hESCs with CHIR and the SHH signaling inhibitor Cyclopamine (CA) for 24 h, but this did not diminish NKX6.1 expression (FIG. 4F). Exogenously added WNT3A (200 ng/mL) could also induce NKX6.1 expression (60±14%) (FIG. 4G), providing further evidence for the involvement of Wnt/β-catenin signaling in this process. In contrast, simultaneous treatment with CHIR and BMP4 (200 ng/mL), a dorsal patterning factor, reduced the expression of NKX6.1 from 91±1% to 68±2% (FIG. 4H). These data collectively indicate that Wnt/β-catenin signaling patterns an initial NKX6.1$^+$ ventral identity during hPSC motor neuron differentiation.

Figures 5A, 5B, 5C, 5D, 5E, 5F, 5G, 5H, 5I:
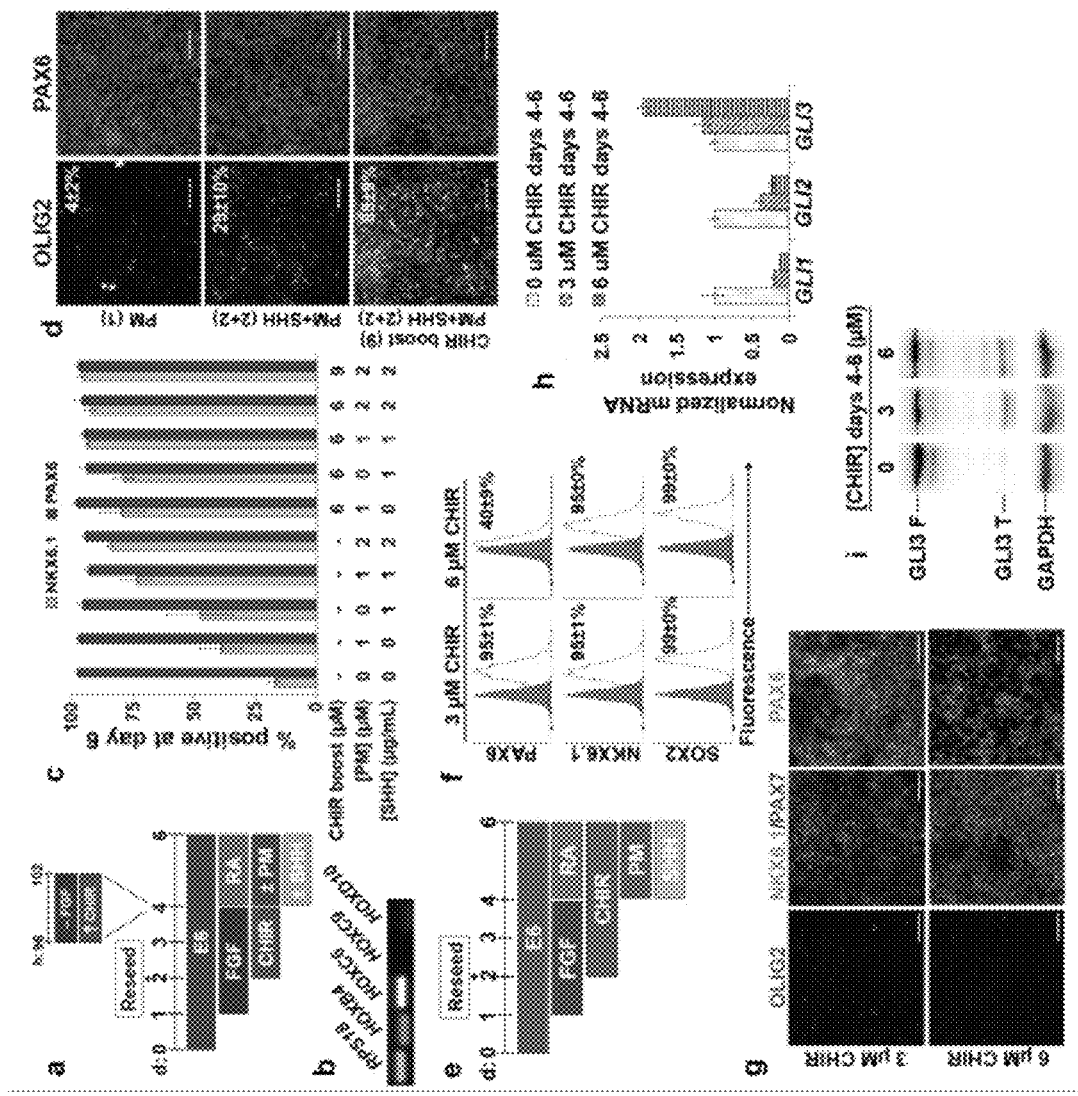
FIG. 5A shows a timeline for optimized induction of OLIG2 expression in panels b-d, in which cultures received a 6 hour CHIR 'boost' in the absence of FGF on day 4 of differentiation prior to adding various combinations of RA, PM, and SHH.
FIG. 5B shows RT-PCR data demonstrating cervical neuroectoderm identity.
FIG. 5C shows NKX6.1 and PAX6 expression quantified by flow cytometry in response to varying concentrations of CHIR, PM, and SHH. [RA]=1 and data and error bars represent mean±S.D. calculated from biological duplicates.
FIG. 5D. OLIG2 expression was quantified relative to PAX6 or DAPI. The numbers in parenthesis adjacent to the images indicate concentrations of the added factors. At least 4 fields were counted per sample (technical replicates, >10$^4$ total cells counted per replicate). Percentages represent mean±S.D. Scale bars, 100 μm. The requirement of a CHIR 'boost' for improved OLIG2 induction was verified across 6 biological replicates.
FIG. 5E presents an experimental timeline for panels f-i, in which CHIR treatment is continued throughout RA (1 μM), (21 μM), and SHH (2 μg/mL) treatment.
FIG. 5F shows flow cytometry analyses of PAX6, NKX6.1, and SOX2 expression in response to varying concentrations of CHIR. Grey histograms, IgG control; red histograms, label of interest. Percentages represent mean±S.D. calculated from two biological replicates.
FIG. 5G shows immunocytochemical analysis of OLIG2, NKX6.1, PAX7, and PAX6 expression in response to varying concentrations of CHIR. Scale bars, 100 μm. OLIG2 and PAX6 images are from the same field.
FIG. 5H shows qPCR comparison of GLI1, GLI2, and GLI3 expression in response to varying concentrations of CHIR. Data are normalized to the 0 μM CHIR condition. Error bars represent mean±S.D. calculated from technical duplicates.
FIG. 5I shows Western blot comparison of GLI3 full length (F; 190 kDa) versus truncated repressor form (T; 83 kDa). For all panels, analyses were conducted on day 6 and the reseed density is 1.5×10$^5$ cells/cm$^2$.

Example 2: Transient Wnt/β-Catenin Followed by RA and SHH Signaling Promotes Efficient Induction of OLIG2$^+$ Motor Neuron Progenitors The rostrocaudal and dorsoventral patterning effects of Wnt/β-catenin can be difficult to decouple. For example, the results described above could be attributed to caudalization of neural progenitors, making them more permissible to enter a ventralized state. To rule out this possibility, the published method for deterministically patterning neuroectoderm along the posterior CNS's rostrocaudal axis (Lippmann, E. S. et al. Deterministic HOX Patterning in Human Pluripotent Stem Cell-Derived Neuroectoderm. Stem Cell Rep. 4, 632-644 (2015)) was used (FIG. 5A). This method relies on Wnt/β-catenin and FGF signaling to direct hPSCs to a SOX2$^+$/Brachyury$^+$ neuromesodermal state that exhibits full collinear HOX activation. Then, at any point during collinear HOX activation, transitioning to RA-containing media halts HOX activation and induces differentiation to PAX6$^+$/SOX2$^+$ neuroectoderm with a predictable and defined rostrocaudal regional identity in the posterior CNS, i.e. discrete HOX expression profile. Since prior motor neuron differentiation methods only generate cells patterned to a single, predominantly cervical spinal region (summarized in Table 1), a merger of Wnt/β-catenin's ventralizing and caudalizing patterning roles could yield the first singular, comprehensive protocol for efficient generation of human OLIG2$^+$ progenitors and post-mitotic motor neurons from any spinal cord region.

TABLE 1

Summary of reported hPSC motor neuron differentiation protocols: efficiency and regional identity.

| Citation | % OLIG2[a] | % Motor neurons[b] | Regional identity[c] |
|---|---|---|---|
| Li et al, 2005 (ref. 22) | N.R. | HB9: ~21% | Cervical |
| Li et al, 2008 (ref. 23) | ~40% | HB9: ~50% | Cervical |
| Lee et al, 2007 (ref. 60) | N.R. | HB9: ~20% | Cervical |
| Karumbayaram et al, 2009 (ref. 24) | 59 ± 7% | ISL1: 34 ± 12% | Cervical |
| Amoroso et al, 2013 (ref. 25) | N.R. | HB9$^+$ISL1: ~51% | Cervical |
| Patani et al, 2011 (ref. 26) | 51 ± 3% | HB9: 18 ± 1 | Variable[d] |
| Chen et al, 2014 (ref. 15) | N.R. | HB9: ~90% | Cervical |
| Kiskinis et al, 2014 (ref. 27) | N.R. | ISL1: 40-50% | Cervical |
| Qu et al, 2014 (ref. 29) | N.R. | HB9: 64 ± 9% ISL1: 76 ± 6% | Cervical |
| Maury et al, 2015 (ref. 14) | ~84% | HB9$^+$ISL1: 74% | Cervical |
| Du et al, 2015 (ref. 16) | 95 ± 3% | HB9: 90 ± 9% ISL1: 95 ± 3% | Cervical |

TABLE 1-continued

Summary of reported hPSC motor neuron differentiation protocols: efficiency and regional identity.

| Citation | % OLIG2[a] | % Motor neurons[b] | Regional identity[c] |
|---|---|---|---|
| Calder et al, 2015 (ref. 28) | ~30% | HB9: ~45% ISL1: ~35% | Cervical |

N.R. = not reported

[a-b]If multiple cell lines and conditions were assayed, we included either the best-performing line or the reported average between all lines. In some cases, percentages were either estimated from graphical data or the number in the text was listed as an approximation.

[c]Regional identity was determined directly from immunocytochemical analysis of HOX expression profiles or inferred from qPCR or high throughput sequencing of HOX expression patterns.

[d]In this study, positive labeling was presented for HOXB4, HOXC9, and HOXC10, but not in the context of motor neuron differentiation, thus preventing regional assignment of motor neurons and assessment of their relative differentiation efficiencies.

To begin, we sequentially differentiated H9 hESCs in E6 media for 1 day, and FGF8b (200 ng/mL) for 1 day, and FGF8b and CHIR (3 µM) for 2 days to generate cervical neuromesoderm (FIGS. 5A-5B). Then, we screened the effects of CHIR, PM, and SHH treatment on NKX6.1$^-$/PAX6$^+$/OLIG2$^+$ motor neuron progenitor induction while transitioning to media containing 1 µM RA (FIGS. 5A-5D). Prior to the addition of RA, NKX6.1 was expressed in the cervical neuromesodermal state at day 4 (80±18% NKX6.1$^+$; data not shown), likely due to the CHIR-induced Wnt/β-catenin signaling (FIGS. 4A-4H). Transitioning the neuromesodermal progenitors to RA-containing media for 2 days induced HOXB4$^+$/HOXC6$^+$/HOXC9$^-$/HOXD10$^-$/PAX6$^+$ cervical neuroectoderm in all conditions (FIGS. 5B-5C), as expected. However, without co-activation of SHH signaling by PM or SHH, NKX6.1 expression was quickly lost by day 6 (97±1% PAX6$^+$, 17±3% NKX6.1$^+$) (FIG. 5C). If CHIR treatment was continued at 3 µM while also adding RA, PM (2 µM), and SHH (2 µg/mL), NKX6.1 and PAX6/SOX2 neuroectoderm markers were uniformly expressed, but minimal OLIG2 was induced by day 6 (FIGS. 5E-5G). Also, if CHIR was increased to 6 µM under the same treatment regime, NKX6.1 and SOX2 were again maintained but PAX6 expression was diminished and OLIG2 was still not induced. In addition, no PAX7 was detected, indicating cells had not shifted towards dorsal identity (FIG. 5G). To investigate why OLIG2 was not induced despite the presence of RA and SHH, we conducted qPCR on day 6 cultures to examine expression levels of GLI transcription factors, which are downstream effectors of SHH signaling. qPCR revealed a >8-fold decrease in GLI1 and >4-fold decrease in GLI2 expression if 6 µM CHIR levels were maintained during RA and PM/SHE exposure, whereas GLI3 was increased by ~2-fold (FIG. 5H). Since GLI1 and GLI2 are classically implicated as transcriptional activators whereas GLI3 is a transcriptional repressor, this data indicates that Wnt/β-catenin activation hinders hedgehog signaling by modulating GLI expression levels. To bolster this claim, we also analyzed the abundance of full-length GLI3 versus its truncated repressor form by western blot. As expected, cultures not treated with CHIR during PM/SHH exposure expressed minimal levels of truncated GLI3 relative to the full-length protein, whereas cultures maintained in 3 and 6 µM CHIR expressed increased levels of the GLI3 truncated repressor form (FIG. 5I). Thus, Wnt/β-catenin signaling is necessary to induce ventral identity, but its continuous activation during OLIG2 induction by SHH signaling is detrimental to motor neuron differentiation, possibly due to activation of the GLI3 repressor.

Next, we tested conditions where CHIR was removed after transitioning to media containing RA (1 µM), PM (2 µM), and SHH (2 µg/mL) (FIGS. 5A-5C). At day 6, NKX6.1$^+$ cells were maintained at 84±1% and PAX6 was again induced at 94±1%, in accordance with a previous report demonstrating the necessity of SHH signaling for maintaining NKX6.1 expression in neural tissue explants in vitro. This result suggests that SHH signaling can sustain a ventral identity after its initial establishment by Wnt/β-catenin signaling.

However, OLIG2 expression was only induced in 29±10% of the overall culture (FIG. 5D). Since NKX6.1 is a pre-requisite to OLIG2 expression, we hypothesized that the Wnt/β-catenin signaling-dependent NKX6.1 expression levels may still be too low for efficient OLIG2$^+$ motor neuron progenitor induction. Therefore, the concentration of CHIR was boosted to 6 or 9 µM for 6 h immediately prior to transitioning to E6 medium containing RA, PM, and SHH without CHIR (FIG. 5A). The 9 µM CHIR boost followed by a transition to media containing 1 µM RA, 2 µM PM, and 2 µg/mL SHH yielded optimal motor neuron progenitor cultures with highly uniform NKX6.1, OLIG2, and PAX6 expression (96±1%, 85±9%, and 97±2%, respectively) (FIGS. 5C-5D).

Figures 6A, 6B, 6C, 6D:
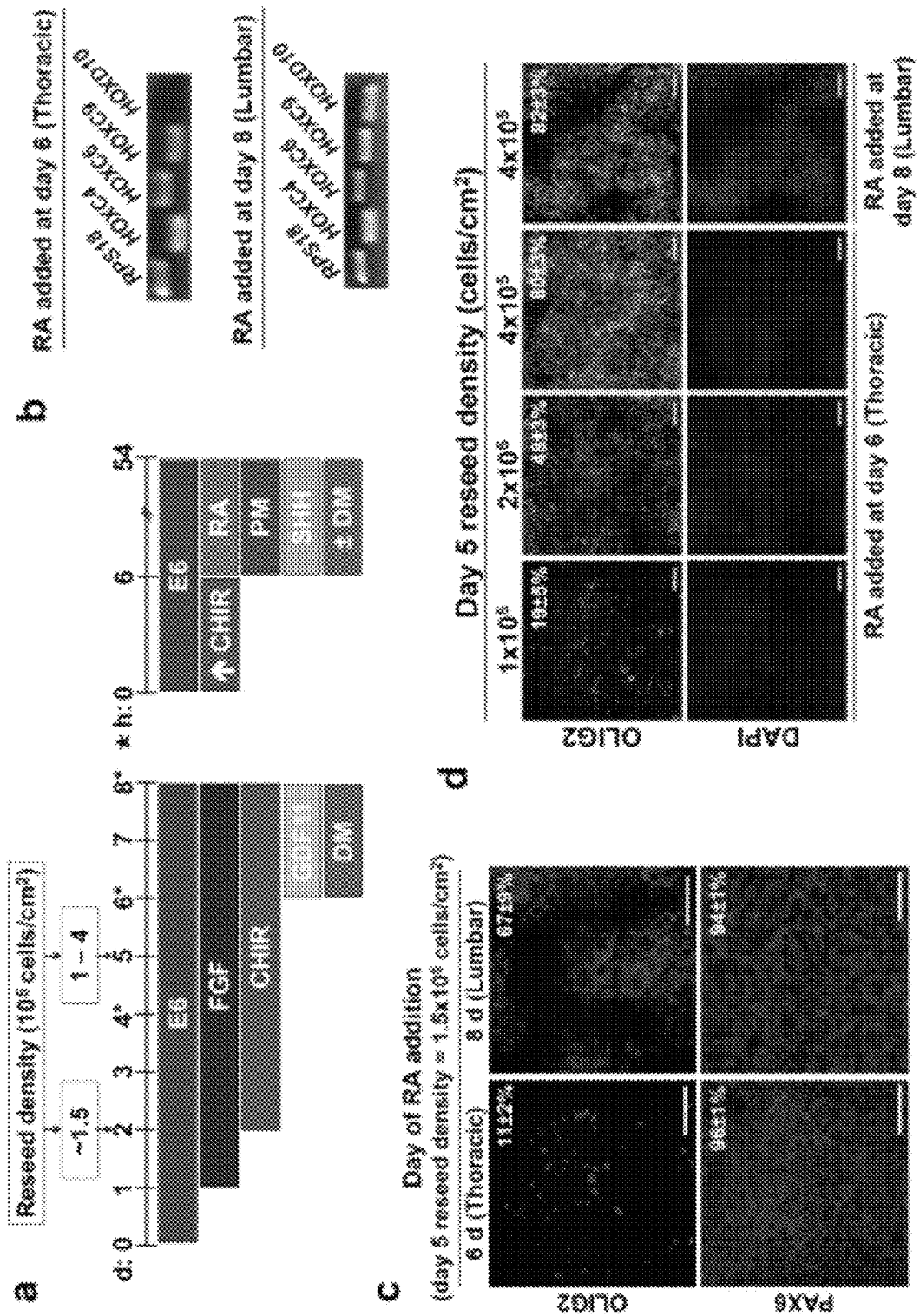
FIGS. 6A-6D. (a) Scheme for derivation of cervical, thoracic, or lumbar cultures. Reseed density on day 2 was approximately 1.5×10$^5$ cells/cm$^2$ and reseed density on day 5 was varied from 1-4×10$^5$ cells/cm$^2$ (see Examples for full details). Asterisks denote transition from caudalization to ventralization procedures. (b) Demonstration of HOXC9$^+$/HOXD10$^-$ thoracic identity and HOXC9$^+$/HOXD10$^+$ lumbar identity by RT-PCR. (c) Immunocytochemical analysis of OLIG2 and PAX6 expression in thoracic and lumbar neuroectoderm using a day 5 reseed density of 1.5×10$^5$ cells/cm$^2$. Expression was quantified relative to DAPI and percentages represent mean±S.D. calculated from technical triplicates (>10$^4$ cells counted per sample). Scale bars, 100 μm. (d) Immunocytochemical analysis of OLIG2 in thoracic and lumbar neuroectoderm using various day 5 reseed densities. Expression was quantified relative to DAPI and percentages represent mean±S.D. calculated from biological triplicates (>10$^4$ cells counted per sample). Scale bars, 100 μm. For all panels, analyses were conducted after 48 h of RA treatment.

Example 3: High Cell Density Effectively Generates OLIG2$^+$ Motor Neuron Progenitors Having demonstrated efficient generation of OLIG2$^+$ motor neuron progenitors at the cervical spinal cord level, the CHIR boost strategy did not yield similar results when patterning OLIG2$^+$ progenitors possessing thoracic and lumbar HOX identity. However, OLIG2 induction was less efficient upon employing the standard deterministic HOX patterning protocol to generate thoracic and lumbar neuromesoderm followed by a CHIR boost and application of RA and SHH/PM (FIG. 6A). Only 11±2% and 67±9% of the cells in the thoracic and lumbar cultures, respectively, were PAX6$^+$/OLIG2$^+$ (FIGS. 6B-6C). We noted that our standard neuromesodermal protocol always used a reseed density of 1.5×10$^5$ cells/cm$^2$, which generates a relatively confluent but not tightly packed cell monolayer 24 h after seeding. Having previously determined that cell density and cell-cell contacts can serve as modulators of neural fate, we explored the effects of seeding density on OLIG2 induction. Indeed, whereas reseeding at 1×10$^5$ cells/cm$^2$ density on day 5 yielded poor OLIG2 induction in thoracic neuroectoderm (19±5%), increasing this density to 2×10$^5$ and 4×10$^5$ cells/cm$^2$ increasingly improved the ability of the CHIR boost and subsequent RA and SHE/PM treatment to generate OLIG2$^+$ cells (48±3% and 80±3% OLIG2$^+$, respectively) (FIGS. 6A-6D). The 4×10$^5$ cells/cm$^2$ reseed density also improved motor neuron progenitor induction efficiency from lumbar neuroectoderm (82±3% OLIG2$^+$), which requires dorsomorphin (DM) supplementation to antagonize GDF11's dorsalizing effects, as discussed prior (FIGS. 6A-6D).

Figures 7A, 7B, 7C:
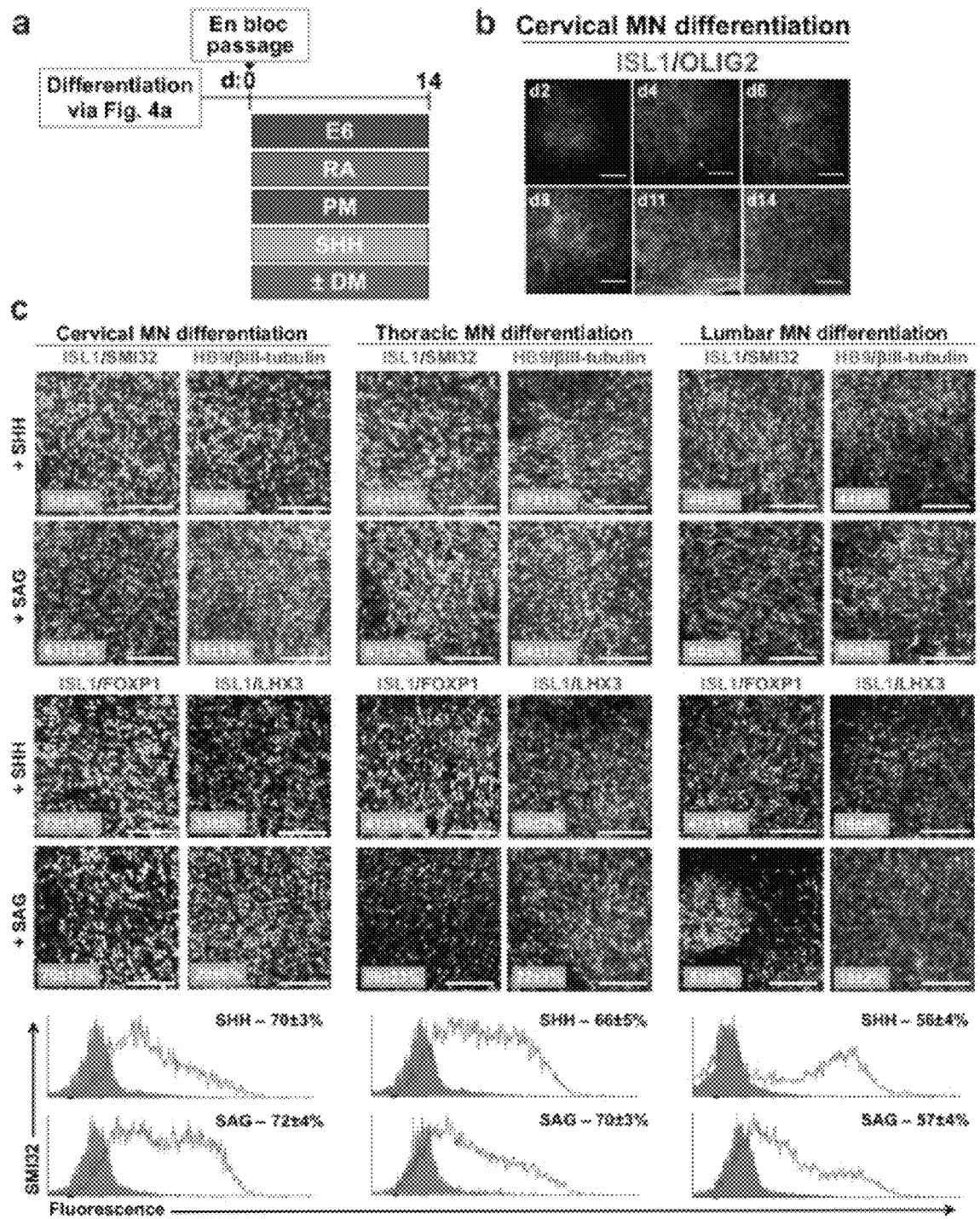
FIGS. 7A-7C. (a) Scheme for differentiation of OLIG2$^+$ progenitors into post-mitotic motor neurons. (b) Temporal transition of cervical OLIG2$^-$ progenitors to ISL1$^-$ motor neurons traced by immunocytochemistry in single colonies after en bloc passage. (c) ISL1$^+$, HB9$^+$, and SMI32$^+$ motor neurons were quantified 14 days after en bloc passage by immunocytochemistry relative to DAPI (blue) or by flow cytometry. Representative images of ISL1$^+$/SMI32$^+$, HB913/βIII-tubulin$^+$, ISL1$^+$/FOXP1$^+$, and ISL1$^+$/LHX3$^+$ motor neurons are shown. Percentages embedded in ISL1/SMI32 and HB9/βIII-tubulin images represent mean±S.D. of ISL1$^+$ or HB9$^+$ cells calculated from biological triplicates (>5,000 total cells counted). Percentages embedded in ISL1/FOXP1 and ISL1/LHX3 images represent mean±S.D. of ISL1$^+$/FOXP1$^+$ or ISL1$^+$/LHX3$^+$ motor neurons quantified relative to total ISL1$^+$ motor neurons and were calculated from biological triplicates (>4,000 total cells counted). SMI32 data are presented as mean±S.D. from biological triplicates. All scale bars, 100 μm.

Example 4: Differentiation to Post-Mitotic Motor Neurons Capable of Forming Neuromuscular Junctions Having optimized the efficiency of OLIG2 induction at diverse spinal cord regions, next region-specific post-mitotic motor neurons were generated. Cervical OLIG2$^+$ motor neuron progenitors were en bloc passaged and gradually differentiated to ISL1$^-$ motor neurons over a 14-day period (FIGS. 7A-7B). After 20 total days of differentiation, cervical motor neuron derivation was found to be highly efficient by quantitative immunocytochemistry and flow cytometry (70±3% SMI32$^+$, 68±8% ISL1$^+$, and 66±4% HB9$^+$) (FIG. 7C). The extensive co-labeling of ISL1$^+$ cells with SMI32-reactive non-phosphorylated neurofilament heavy chain is indicative of motor neuron identity. Widespread HB9/βIII-tubulin motor neuron expression was also observed throughout the cultures (FIG. 7C). Since spinal motor neurons in vivo are observed to be both ISL1$^+$, ISL1$^+$/HB9$^+$, and HB9$^+$ but are all SMI32 reactive, flow cytometry of the SMI32$^+$ cells is proposed to best represent the total percentage of motor neurons in each culture. Moreover, the use of SAG (2 μM), a small molecule Smoothened agonist45, instead of SHE yielded similar efficiencies (72±4% SMI32$^+$, 63±13% ISL1$^+$, and 65±15% HB9$^+$) (FIG. 7C). High efficiencies were also observed for thoracic cultures, whereas lumbar cultures saw a ~10% decrease in efficiency (FIG. 7C). For all regions, ISL1$^+$ motor neurons predominantly co-labeled with FOXP1 (70-80% in cervical motor neurons and 40-60% in thoracic and lumbar motor neurons) versus LHX3 markers (20-30% in cervical and thoracic cultures and 15-20% in lumbar cultures) (FIG. 7C). This suggests that our derivation protocol generates motor neurons with a lateral motor column phenotype bias in the cervical and lumbar regions, whereas a more balanced distribution between preganglionic or hypaxial motor column versus medial motor column motor neuron phenotypes is observed in the thoracic region. These trends agree with the observed distribution of columnar motor neuron phenotype in the cervical, thoracic and lumbar spinal cord in vivo, and it is consistent with our prior observations of motor neuron populations derived using the deterministic HOX patterning protocol.

Figures 8A, 8B, 8C:
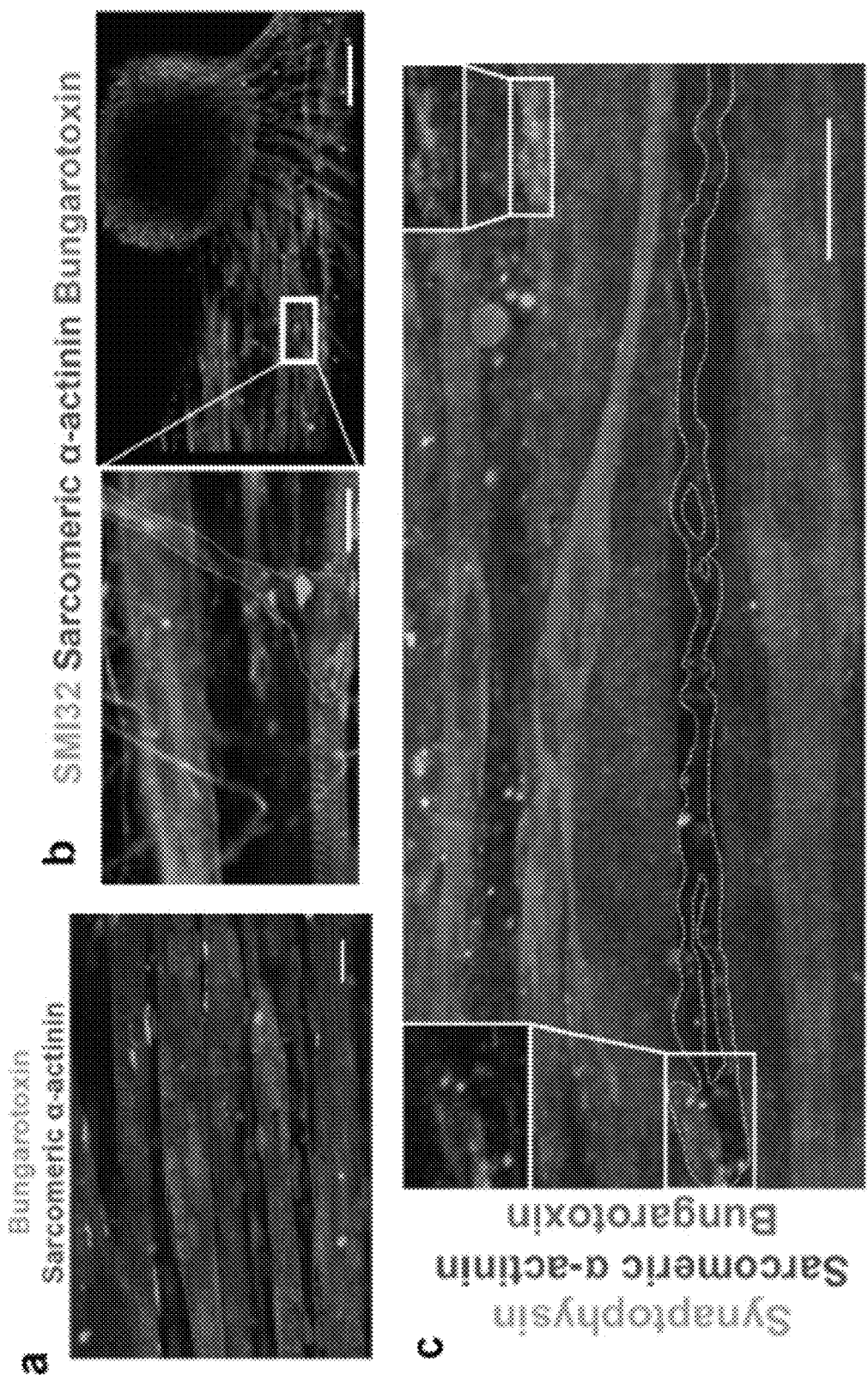
FIGS. 8A-8C. (a) Immunocytochemical detection of bungarotoxin-labeled acetylcholine receptor clusters on sarcomeric α-actinin$^+$ striated skeletal muscle fibers in the absence of motor neurons. Scale bar, 25 μm. (b) Three-dimensional human skeletal muscle tissue co-cultured with a cluster of cervical motor neurons. Dotted white lines trace the path of individual SMI32$^+$ neurites from the motor neuron cluster to the muscle fiber. Hoechst nuclear stain is overlaid in blue. Left scale bar, 15 μm; right scale bar, 100 μm. (c) Presumptive neuromuscular junction formation indicated by co-localization of bungarotoxin and synaptophysin on a striated muscle fiber. Insets provide a magnified view of synaptophysin$^+$ (green) vesicles accumulated at acetylcholine receptor clusters (magenta). Dotted white lines trace the path of individual synaptophysin$^+$ neurites from the motor neuron cluster. Hoechst nuclear stain is overlaid in blue. Scale bar, 20 μm. For these experiments, cervical motor neuron differentiation was conducted according to FIG. 5A with minor modifications.
Figure 9:
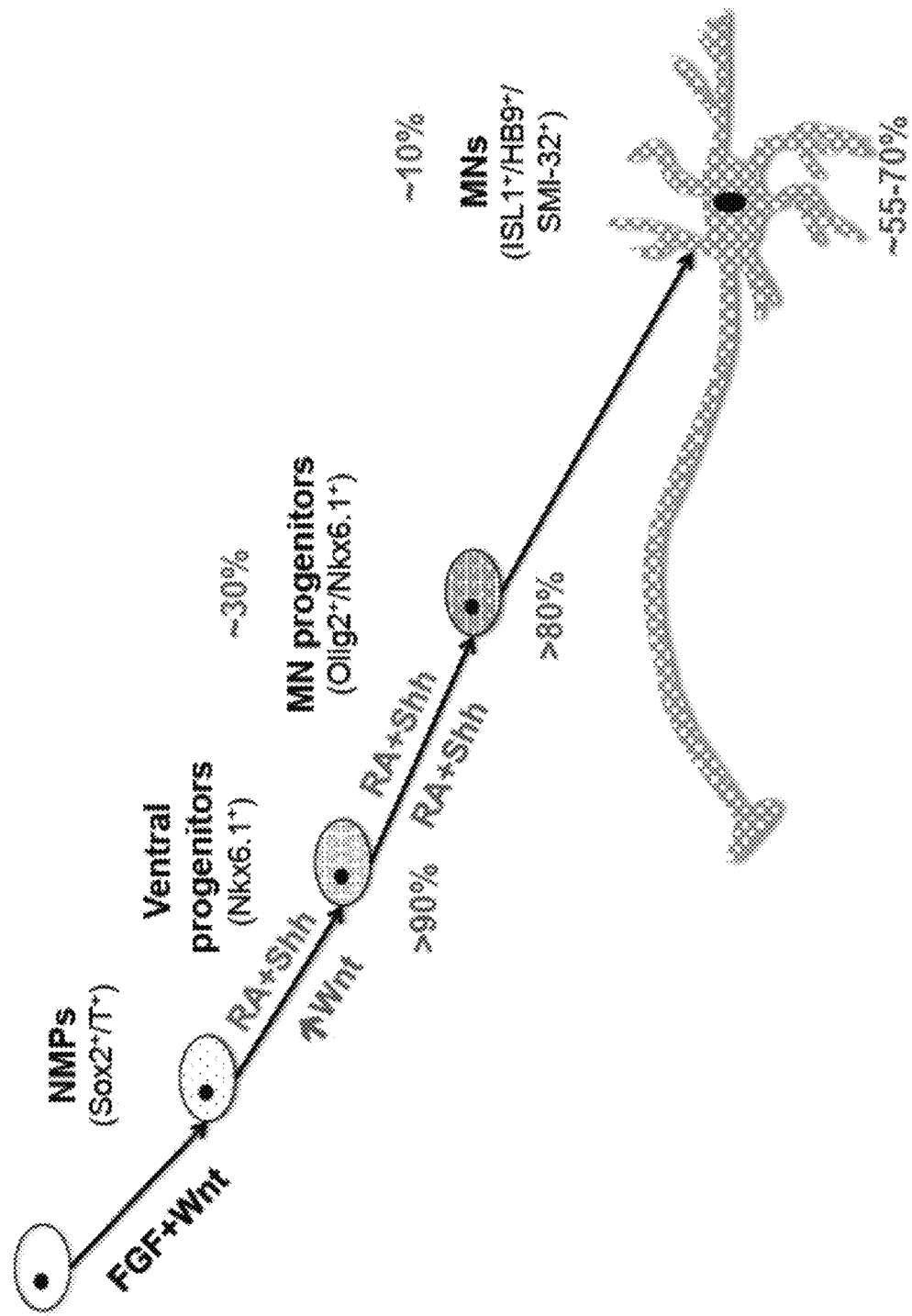
FIG. 9 depicts an overall summary of the process, showing the higher percentage efficiencies with which each cell type is obtained relative to the method disclosed in incorporated U.S. patent application Ser. No. 14/496,796 (published as 2016/0068806).

Cervical motor neurons were co-cultured with primary human myoblasts to determine if they could innervate muscle fibers and form neuromuscular junctions. After 10 days of co-culture, co-localization of SMI32$^+$ and synaptophysin$^+$ neuronal processes with bungarotoxin labeled acetylcholine receptor clusters on and sarcomeric α-actinin$^+$ skeletal muscle fibers were observed, indicating neuromuscular junction formation (FIGS. 8A-8C). Also, we previously demonstrated that similarly derived ISL1$^-$, HB9$^+$, and SMI32$^+$ motor neurons could fire action potentials upon extended maturation. Collectively, these results indicate a successful merger of Wnt/β-catenin signaling's ventralizing and caudalizing roles to develop a singular, comprehensive protocol for efficiently differentiating hPSCs into OLIG2$^+$ motor neuron progenitors and post-mitotic motor neurons from any spinal cord region (FIGS. 6A and 7A, and summarized in FIG. 9).

Figure 10:
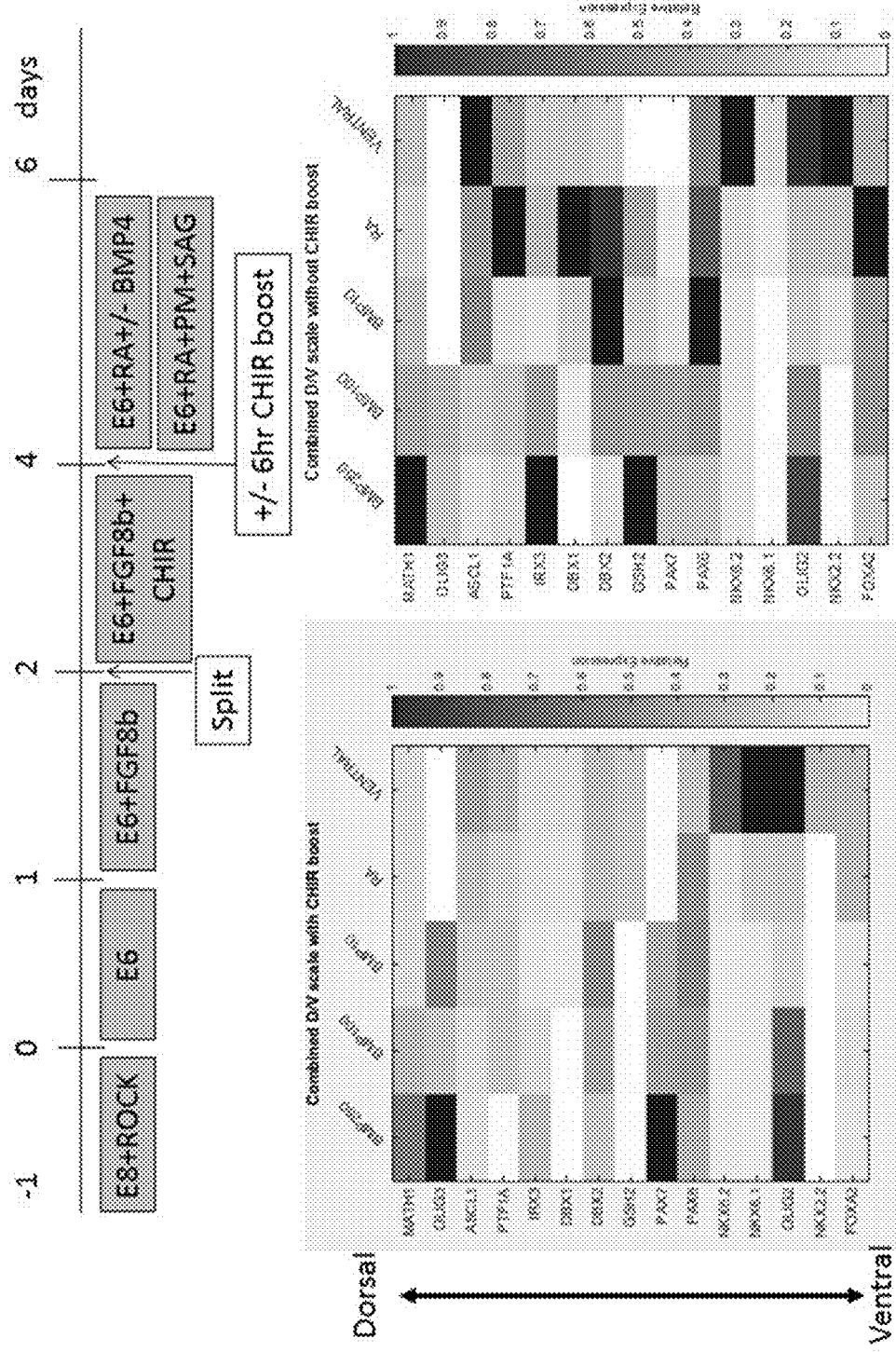
FIG. 10 demonstrates that a Wnt signaling boost specifically enhances ventral motor neuron progenitor gene expression. Quantitative PCR analysis was performed on human pluripotent stem cells differentiated into diverse neuronal progenitors populations (Day 6), spanning the dorsoventral axis of the developing spinal cord, in the presence or absence of a transient six-hour boost in Wnt signaling. "Ventral"=1 μM Retinoic Acid+2 μM Purmorphamine & SAG (small molecule Smoothened agonist); "RA"=1 μM Retinoic Acid; "BMP 10/100/250": 1 μM Retinoic Acid+10, 100, or 250 ng/mL Bone Morphogenetic Protein 4. Under "Ventral" differentiation conditions, the presence of a transient Wnt boost on day 4 specifically increased expression of motor neuron progenitor genes (Olig2/Nkx 6.1), whereas upregulation of genes indicating ventral p3 progenitors (Nkx2.2/Nkx6.2) and p1/2 progenitors (Nkx6.2) occurred in the absence of the transient Wnt signaling boost. This indicates that the Wnt boost specifically enhances motor neuron progenitor derivation.

As demonstrated in FIG. 10, Wnt signaling boost enhances ventral motor neuron progenitor gene expression specifically. Quantitative PCR analysis was performed on diverse neuronal progenitors populations (Day 6) differentiated from human pluripotent stem cells in the presence or absence of a transient boost in Wnt signaling. The neuronal progenitor spanned the dorsoventral axis of the developing spinal cord. In 'Ventral' differentiation conditions, the presence of a Wnt boost increased expression of motor neuron progenitor genes (Olig2/Nkx 6.1) specifically, whereas upregulation of genes indicating ventral p3 (Nkx2.2/Nkx6.2) and p1/2 progenitors (Nkx6.2) occurred in the absence of a transient Wnt signaling boost. This indicates that the Wnt boost specifically enhances motor neuron progenitor derivation.

Materials and Methods hESC Maintenance hESCs were maintained on Matrigel (BD Biosciences) in E8 medium but with 10-fold lower insulin concentration (2 mg/L). Cell lines used in this study were H9 hESCs (passage 25-45) and H9 ishcat2 hESCs (passage 35-45). Doxycycline (2 μg/ml; Sigma) was used for induction of β-catenin knockdown in the ishcat2 line.

Differentiation to Motor Neurons hESCs were dissociated with accutase (Thermo Fisher Scientific) and reseeded at 1×10$^5$ cells/cm2 in E8 medium containing 10 μM ROCK inhibitor (Y27632; R&D Systems) on 6-well polystyrene tissue culture plates coated with 100 μg/mL poly-L-ornithine (PLO; Sigma) and 8 μg/well VTN-NC. The timelines and relevant growth factors/small molecules for all differentiation procedures are described in detail in the Results section and its accompanying figures. Cells were differentiated for various amounts of time in E6 medium containing the same insulin concentration as E8 medium as described above with varying combinations of soluble factors (product information and concentration ranges are found in Table 2). For neuromesodermal induction and HOX propagation, cells were sequentially cultured with FGF8b, CHIR99021 (CHIR), GDF11, and dorsomorphin (DM) as previously described. Briefly, to initiate the neuromesodermal state, cells were changed to E6 medium followed by addition of FGF8b (200 ng/ml) 24 h later. To generate cervical neuromesodermal progenitors, cells were washed with PBS, treated with accutase, and re-seeded in E6 medium containing 200 ng/ml FGF8b, 3 μM CHIR, and 10 μM Y27632 on VTN-NC-coated plates at a density of 1.5×10$^5$ cells/cm$^2$ for 48 h. To generate thoracic neuromesodermal progenitors, cells were passaged again after 72 h of CHIR treatment and re-seeded at different densities as described in the text.

Thoracic identity was reached after an additional 24 h. Then, to reach the lumbosacral level, cells were given 30 ng/ml GDF11 and 1 μM DM for an additional 48 h. For neuroectoderm induction and generation of OLIG2$^+$ progenitors, FGF8b was removed at the designated time points and the concentration of CHIR was increased for 6 h as described in the text, followed by a transition to media containing RA, PM, and SHH for a period of 48 h. For differentiation of the OLIG2$^+$ progenitors to motor neurons, cells were subcultured by en bloc passage using a cell scraper, reseeded at a 1:200 ratio in Matrigel-coated 8-well chamber slides, and differentiated for 14 days in E6 medium containing 1 μM RA, 100 nM PM, and 100 ng/mL SHH, with media exchange every 3 days (10 μM Y27632 was included during the en bloc passaging step and removed after the first media exchange). For differentiation of lumbar cultures, 1 μM DM was included in all steps. For the myoblast co-culture experiments, OLIG2$^+$ cultures were en bloc passaged, frozen in E6 medium containing 10% DMSO, shipped to a different location, and thawed 1:10 in 6-well plates under the same conditions as described in FIG. 5. To facilitate neuronal maturation prior to myoblast co-culture, 5 μM DAPT (Tocris) was added from days 8-14 post-thaw. Flow cytometry, RT-PCR, and qPCR (RPS18 and CTNNB1 Taqman primers from Thermo Fisher Scientific) were conducted as previously described.

Human Skeletal Muscle Cell Isolation and Culture

Human skeletal muscle tissue removed in the course of scheduled surgical procedures and designated for disposal was utilized in this study in accordance with Mount Sinai Hospital research ethics board approval and University of Toronto administrative ethics review approval. Primary myoblast and fibroblast cell lines were established and maintained as previously described (Webster et al., *Exp Cell*

Res. 1988; 174:252-265). Briefly, human skeletal muscle samples were minced and then dissociated into a single cell slurry with Clostridium histolyticum collagenase (Sigma) diluted to 630 U/mL in Dulbecco's modified eagle medium (DMEM; Sigma). The cell suspension was passed multiple times through a 20 G needle to facilitate release of the mononucleated cell population and subsequently depleted of red blood cells with a brief incubation in red blood cell lysis buffer (15.5 mM $NH_4Cl$, 1 mM $KHCO_3$, 10 mM EDTA). The resulting cell suspension containing a mixed population of myoblasts and fibroblasts was plated in a collagen-coated tissue culture dish containing myoblast growth medium: F-10 media (Thermo Fisher Scientific), 20% fetal bovine serum (Gibco), 5 ng/ml basic fibroblast growth factor (bFGF; ImmunoTools) and 1% penicillin streptomycin (Thermo Fisher Scientific). After one passage, the cell culture mixture was stained with an antibody recognizing the neural cell adhesion molecule (NCAM/CD56; BD Pharmingen), and the myogenic progenitor (CD56+) and fibroblast (CD56-) populations were separated and purified using fluorescence-activated cell sorting (FACS). Subsequent experiments utilized low passage cultures between P4 and P9.

In Vitro Generation of Innervated Human Skeletal Muscle Tissues

[000102] Three-dimensional skeletal muscle tissues were generated in culture as previously described (Madden et al., eLife. 2015; 4:e04885) with one modification: FACS-purified myoblast and fibroblast cells were incorporated into tissues at established ratios as follows. CD56+ (95%) and CD56- (5%) cells were resuspended in a fibrinogen (Sigma)/Matrigel® (Thermo Fisher Scientific) matrix. Thrombin (Sigma) was added at 0.5 unit per mg of fibrinogen just prior to seeding the cell/matrix suspension into a custom-made device designed to impose uniaxial tension and was then incubated for 15 min at 37° C. to expedite fibrin/Matrigel® polymerization. Next, a 14-day post-thaw neuronal cluster derived according to the Methods section was detached using a pipette tip and transferred atop the polymerized matrix in myoblast growth media lacking bFGF but containing 2 mg/ml 6-aminocaproic acid (ACA; Sigma), 10 ng/mL BDNF, and 10 ng/mL GDNF. The culture media was exchanged 2 days later to a formulation that supports myogenic differentiation (DMEM+2% horse serum (Gibco)+10 µg/ml insulin (Sigma)+1% penicillin-streptomycin) and also containing 2 mg/ml ACA, 10 ng/ml BDNF, and 10 ng/ml GDNF. Half of the culture media was exchanged every other day thereafter. Cells were analyzed after 10 days of co-culture.

Immunocytochemistry

Immunocytochemistry was performed on tissue culture plates and chamber slides as previously described (Lippmann et al., Stem Cells. 2014; 32:1032-1042). Quantification was carried out by manual counting and/or using CellProfiler software (Carpenter et al., Genome Biol. 2006; 7:R100). For innervated skeletal muscle tissues, the constructs were fixed in 4% PFA for 30 min at room temperature and then permeabilized with 0.5% Triton X-100 in PBS. Tissues were blocked in PBS containing 20% goat serum for at least 1 h at room temperature and then incubated with primary monoclonal antibodies to sarcomeric α-actinin, synaptophysin, and SMI-32 overnight at 4° C. The next day, tissues were washed thoroughly and then incubated with appropriate secondary antibodies, Alexa Fluor 647 conjugated α-bungarotoxin (Thermo Fisher Scientific, 1:200), and Hoechst (Thermo Fisher Scientific) for 30 min at room temperature. Following extensive washing, confocal images of stained tissues were obtained using Fluoview software with an Olympus IX83 inverted microscope equipped with a DP80 dual CCD camera.

Western Blotting

Cells were washed with cold PBS, harvested with accutase, and pelleted by centrifugation. The pellets were lysed on ice for 30 min in lysis buffer composed of 150 mM NaCl, 50 mM Tris pH 7.4, 5 mM EDTA, 0.5% NP-40, 0.5% sodium deoxycholate, and Halt protease inhibitor cocktail (Thermo Fisher Scientific). Lysates were then subjected to a freeze/thaw cycle. The cell lysates were centrifuged for 10 min at 2000 g at 4° C. and the supernatants were used for immunoblotting. Protein concentration was estimated by micro bicinchoninic acid (BCA) assay (Thermo Fisher Scientific). Samples were resolved on SDS-PAGE gels, blotted on nitrocellulose membranes, and blocked with 10 mM Tris pH 7.5, 0.15 M NaCl, 0.05% (v/v) Tween 20, and 5% non-fat dry milk. The blot was incubated overnight with a GLI3 antibody, followed by washes and a 2 h incubation with an anti-rabbit IgG conjugated to horseradish peroxidase (Thermo Fisher Scientific). Immunostained bands were detected using the SuperSignal West Pico Chemiluminescent Substrate kit (Thermo Fisher Scientific). The blot was then stripped and the process repeated with the GAPDH antibody.

Antibody descriptions are located in Table 3 and primer sequences are located in Table 4.

TABLE 2

Small molecule and growth factor information.

| Soluble factor | Concentration | Vendor |
| --- | --- | --- |
| CHIR99021 (CHIR) | 3-6 µM | Tocris |
| FGF8B | 200 ng/mL | Peprotech |
| GDF11 | 30 ng/mL | Peprotech |
| Dorsomorphin dihydrochloride (DM) | 1 µM | Tocris |
| Purmorphamine (PM) | 0.1-2 µM | Cayman Chemical or Tocris |
| Sonic hedgehog (SHH) | 0.1-2 µg/mL | Produced in-house as previously described (Wall et al. Bioconjug Chem. 2008; 19: 806-812) |
| Retinoic acid (RA) | 1 µM | Sigma |
| WNT3A | 200 ng/mL | Peprotech |
| Brain-derived neurotrophic factor (BDNF) | 10 ng/mL | Peprotech |
| Glial-derived neurotrophic factor (GDNF) | 10 ng/mL | Peprotech |
| cAMP | 1 µM | Sigma |
| Cyclopamine (CA) | 5 µM | Cayman Chemical |
| BMP4 | 200 ng/mL | Peprotech |
| DAPT | 5 µM | Tocris |

TABLE 3

Primary antibody information.

| Antigen | Host species | Clone or product # | Dilution | Vendor |
| --- | --- | --- | --- | --- |
| SOX2 | Mouse | 10H9.1 | 1:1000 (FC) | Millipore |
| Pax6 | Mouse | N/A | 1:200 (FC) 1:50 (ICC) | DSHB |
| Pax7 | Mouse | N/A | 1:100 (ICC) | DSHB |
| OLIG2 | Rabbit | AB9610 | 1:250 (ICC) | Millipore |
| NKX6.1 | Goat | AF5857 | 1:200 (FC) 1:200 (ICC) | R&D Systems |
| NKX6.1 | Mouse | F55A12 | 1:1000 (FC) | DSHB |
| HB9 | Mouse | 81.5C10 | 1:50 (ICC) | DSHB |
| ISL1 | Goat | AF1837 | 1:500 (ICC) | R&D Systems |
| FOXP1 | Rabbit | ab16645 | 1:20000 (ICC) | Abcam |

TABLE 3-continued

Primary antibody information.

| Antigen | Host species | Clone or product # | Dilution | Vendor |
|---|---|---|---|---|
| LHX3 | Mouse | 67.4E12 | 1:100 | DSHB |
| NF-H (SMI32) | Mouse | SMI-32R | 1:1000 (ICC)* 1:200 (ICC)* | Covance |
| βIII-tubulin | Rabbit | PRB-435P | 1:1000 (ICC) | Covance |
| Sarcomeric α-actinin | Mouse | ab9465 | 1:200 (ICC) | Abcam |
| Synaptophysin | Mouse | ab8049 | 1:50 (ICC) | Abcam |
| GLI3 | Rabbit | ab69838 | 1:500 (WB) | Abcam |
| GAPDH | Rabbit | ab9485 | 1:2000 (WB) | Abcam |

*For NF-H ICC, the 1:1000 dilution was used when labeling motor neurons alone and the 1:200 dilution was used when labeling motor neuron/myoblast co-cultures.

TABLE 4

RT-PCR primer information.

| Gene | Primer sequence | Cycles/$T_{annealing}$ (° C.) |
|---|---|---|
| GAPDH | F: CACCGTCAAGGCTGAGAACG (SEQ ID NO: 1) R: GCCCCACTTGATTTTGGAGG (SEQ ID NO: 2) | 35/55 |
| NKX6-1 | F: ACACGAGACCCACTTTTTCCG (SEQ ID NO: 3) R: TGCTGGACTTGTGCTTCTTCAAC (SEQ ID NO: 4) | 35/55 |
| OLIG2 | F: AAGGAGGCAGTGGCTTCAAGTC (SEQ ID NO: 5) R: CGCTCACCAGTCGCTTCATC (SEQ ID NO: 6) | 35/55 |

Note:
in FIGS. 3A-3C and FIGS. 4A-4H, Taqman primers (Thermo Fisher Scientific) for RPS18, HOXB4, HOXC4, HOXC6, HOXC9, and HOXD10 were utilized for RT-PCR.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

What is claimed is:

1. A method for generating motor neuron progenitor cells, comprising the steps of:
   i. culturing an adherent monolayer of SOX2$^+$ and Brachyury$^+$ neuromesodermal progenitor cells in a neural differentiation base medium that comprises FGF and a first concentration of a Wnt/β-catenin signaling pathway agonist for about 4 days;
   ii. transiently exposing the cultured cells of (i) to a second concentration of the Wnt/β-catenin signaling pathway agonist for about 6 hours whereby NKX6.1$^+$ ventral progenitor cells are obtained, wherein the second concentration is at least two times greater than the first concentration;
   iii. replacing the neural differentiation base medium comprising the second higher concentration of the Wnt/β-catenin signaling pathway agonist with a neural differentiation base medium supplemented with a retinoid and at least one sonic hedgehog (SHH) signaling pathway agonist and lacking any Wnt/β-catenin signaling pathway agonist; and
   iv. culturing the NKX6.1$^+$ ventral progenitor cells in the neural differentiation base medium of (iii) for about 2 days whereby a cell population comprising at least 80% OLIG2+ motor neuron progenitors, at least 95% NKX6.1+ motor neuron progenitors, and at least 95% Pax6+ motor neuron progenitors is obtained about 6 days from the start of step (i).

2. The method of claim 1, wherein the Wnt/β-catenin signaling pathway agonist is CHIR99021, and wherein the first concentration is about 3 μM and the second higher concentration is in the range of about 6-9 μM.

3. The method of claim 1, wherein NKX6.1$^+$ ventral progenitor cells have a cervical identity or a hindbrain identity.

4. The method of claim 2, wherein the NKX6.1$^+$ ventral progenitor cells having a cervical identity are generated with at least 90% efficiency from the neuromesodermal progenitor cells.

5. The method of claim 1, wherein OLIG2$^+$, NKX6.1$^+$, and PAX6$^+$ motor neuron progenitor cells are generated with at least 80% efficiency from the NKX6.1$^+$ ventral progenitor cells.

6. The method of claim 1, wherein the Wnt/β-catenin signaling pathway agonist is selected from the group consisting of Wnt-3a and a glycogen synthase kinase 3 (GSK3) inhibitor, wherein the GSK3 inhibitor is selected from the group consisting of CHIR99021, CHIR98014, BIO-acetoxime, BIO, LiCl, SB216763, SB415286, AR A014418, 1-Azakenpaullone, and Bis-7-indolylmaleimide.

7. The method of claim 1, wherein the SHH signaling pathway agonist is selected from the group consisting of purmorphamine (PM), SHH, and a combination thereof.

8. The method of claim 1, wherein the neuromesodermal progenitor cells are cultured at a cell density of about $2\times10^5$ to about $4\times10^5$ cells/cm$^2$ to maintain a confluent but not tightly packed cell monolayer.

9. The method of claim 8, wherein the NKX6.1$^+$ ventral progenitor cells have a thoracic identity.

10. The method of claim 8, wherein the medium in which the NKX6.1$^+$ ventral progenitor cells are cultured further comprises a Growth Differentiation Factor (GDF) and an inhibitor of BMP signaling.

11. The method of claim 10, wherein the inhibitor of BMP signaling is dorsomorphin.

12. The method of claim 10, wherein the motor neuron progenitor cells have a lumbar identity.

13. The method of claim 1, wherein the neuromesodermal progenitor cells are obtained by culturing human pluripotent stem cells as an adherent monolayer in the presence of the Wnt/β-catenin signaling pathway agonist and FGF in the neural differentiation base medium until the neuromesodermal progenitor cells are obtained.

14. The method of claim 1, wherein the neural differentiation base medium is selected from the group consisting of E4, E5, and E6 medium.

15. The method of claim 1, wherein the retinoid is retinoic acid.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: GAPDH Forward

<400> SEQUENCE: 1
caccgtcaag gctgagaacg                                              20

<210> SEQ ID NO 2
<211> LENGTH: 20
<212> TYPE: DNA
<213> ORGANISM: Artificial Sequence
<220> FEATURE:
<223> OTHER INFORMATION: GAPDH Reverse

<400> SEQUENCE: 2
gccccacttg attttggagg                                              20

<210> SEQ ID NO 3
<211> LENGTH: 21
<212> TYPE: DNA
<213> ORGANISM: Artificial Sequence
<220> FEATURE:
<223> OTHER INFORMATION: NKX6-1 Forward

<400> SEQUENCE: 3
acacgagacc cactttttcc g                                            21

<210> SEQ ID NO 4
<211> LENGTH: 23
<212> TYPE: DNA
<213> ORGANISM: Artificial Sequence
```

```
<220> FEATURE:
<223> OTHER INFORMATION: NKX6-1 Reverse

<400> SEQUENCE: 4
tgctggactt gtgcttcttc aac                                             23

<210> SEQ ID NO 5
<211> LENGTH: 22
<212> TYPE: DNA
<213> ORGANISM: Artificial Sequence
<220> FEATURE:
<223> OTHER INFORMATION: OLIG2 Forward

<400> SEQUENCE: 5
aaggaggcag tggcttcaag tc                                              22

<210> SEQ ID NO 6
<211> LENGTH: 20
<212> TYPE: DNA
<213> ORGANISM: Artificial Sequence
<220> FEATURE:
<223> OTHER INFORMATION: OLIG2 Reverse

<400> SEQUENCE: 6
cgctcaccag tcgcttcatc                                                 20
```